(12) United States Patent
Sekimoto

(10) Patent No.: US 11,215,551 B2
(45) Date of Patent: Jan. 4, 2022

(54) VIABLE PARTICLE COUNTING SYSTEM AND VIABLE PARTICLE COUNTING METHOD

(71) Applicant: RION CO., LTD., Kokubunji-Shi (JP)

(72) Inventor: Kazuma Sekimoto, Kokubunji-Shi (JP)

(73) Assignee: RION CO., LTD., Tokyo (JP)

( * ) Notice: Subject to any disclaimer, the term of this patent is extended or adjusted under 35 U.S.C. 154(b) by 1205 days.

(21) Appl. No.: 14/766,578

(22) PCT Filed: Jan. 20, 2014

(86) PCT No.: PCT/JP2014/000252
§ 371 (c)(1),
(2) Date: Aug. 7, 2015

(87) PCT Pub. No.: WO2014/122889
PCT Pub. Date: Aug. 14, 2014

(65) Prior Publication Data
US 2015/0346077 A1    Dec. 3, 2015

(30) Foreign Application Priority Data
Feb. 8, 2013    (JP) .............................. JP2013-023189

(51) Int. Cl.
*G01N 15/14* (2006.01)
*G01N 21/64* (2006.01)

(52) U.S. Cl.
CPC ..... *G01N 15/1436* (2013.01); *G01N 15/1459* (2013.01); *G01N 21/6486* (2013.01); *G01N 2015/1486* (2013.01)

(58) Field of Classification Search
CPC ....... G01N 2015/1438; G01N 15/1436; G01N 15/1459
(Continued)

(56) References Cited

U.S. PATENT DOCUMENTS

| 5,206,699 A | 4/1993 | Stewart et al. |
| 5,351,117 A | 9/1994 | Stewart et al. |

(Continued)

FOREIGN PATENT DOCUMENTS

| JP | H02-085750 A | 3/1990 |
| JP | H06-046360 U | 6/1994 |

(Continued)

*Primary Examiner* — David P Porta
*Assistant Examiner* — Carolyn Fin
(74) *Attorney, Agent, or Firm* — Rankin, Hill & Clark LLP

(57) ABSTRACT

A particle counting system includes a particle counting means and pre-stage irradiation means. The particle counting means counts particles existing in a fluid by irradiating the fluid containing target particles with light at a predetermined wavelength, separating selectively autofluorescence or phosphorescence emitted from the target particles by the radiated light, receiving the separated autofluorescence or phosphorescence, and determining that the target particles are the particles according to the received autofluorescence or phosphorescence. The pre-stage irradiation means irradiates the fluid with ultraviolet light in advance before the particle counting means irradiates the fluid with the light at the predetermined wavelength. The particle counting means includes a band-pass filter that allows light having a wavelength of 450 nm to 600 nm to pass therethrough.

16 Claims, 15 Drawing Sheets

(58) Field of Classification Search
USPC ............. 250/461.1, 362, 364, 373, 393, 395
See application file for complete search history.

(56) References Cited

U.S. PATENT DOCUMENTS

| | | | |
|---|---|---|---|
| 5,444,807 A * | 8/1995 | Liu ........................ | G01N 30/74 204/452 |
| 2010/0108910 A1 | 5/2010 | Morrell et al. | |
| 2013/0015362 A1 * | 1/2013 | Hooper .............. | G01N 15/1434 250/372 |
| 2013/0207007 A1 * | 8/2013 | Tanabe ............... | G01N 21/6458 250/573 |
| 2014/0335557 A1 | 11/2014 | Ichijyo et al. | |

FOREIGN PATENT DOCUMENTS

| | | | |
|---|---|---|---|
| JP | 2003-038163 A | 2/2003 |
| JP | 2003-169695 A | 6/2003 |
| JP | 2005-308414 A | 11/2005 |
| JP | 2009-501907 A | 1/2009 |
| JP | 2012-217382 A | 11/2012 |
| WO | 2007/011854 A2 | 1/2007 |
| WO | 2013/084444 A1 | 6/2013 |

* cited by examiner

FIG. 14

MEDIUM-SIZED YELLOW COLONY

Legend:
- ♦ SCATTERED CUMU (0.2μm OR MORE)
- ■ FLUORESCENCE CUMU (0.2μm OR MORE)
- ◀ 0.2 TO 0.4μm SCATTERED
- ○ 0.4 TO 0.6μm SCATTERED
- ✳ 0.6 TO 0.8μm SCATTERED
- ● 0.8 TO 1.0μm SCATTERED
- ✱ 1.0μm OR MORE SCATTERED X-axis: UV-C IRRADIATION TIME (0min to 31min)
Y-axis: COUNTED VALUE [PARTICLES/10ml] (0 to 20000)

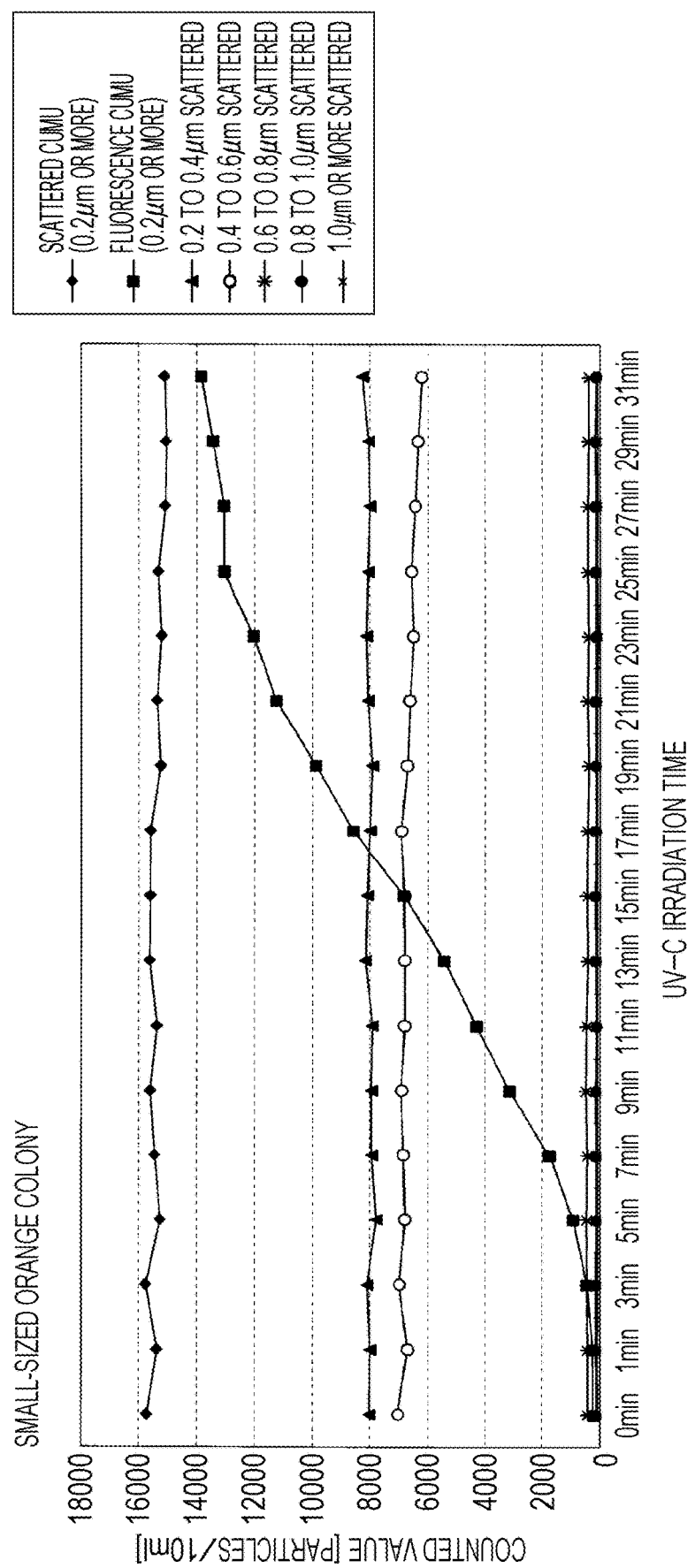

VIABLE PARTICLE COUNTING SYSTEM AND VIABLE PARTICLE COUNTING METHOD

CROSS REFERENCE TO RELATED APPLICATIONS

The present application is the U.S. National Phase of International Patent Application Serial No. PCT/JP2014/000,252, filed Jan. 20, 2014, which claims priority to Japanese Patent Application Serial No. 2013-023189, filed Feb. 8, 2013. The contents of the foregoing applications are incorporated by reference in their entireties.

TECHNICAL FIELD

This invention relates to a viable particle counting system and a viable particle counting method that are configured to detect viable particles in the air or a liquid according to autofluorescence or phosphorescence emitted from the viable particles.

BACKGROUND ART

There are conventionally known methods for detection of viable particles such as a cultivation method (official method), a microcolony method, an ATP (luciferase) method, a fluorescent dye method, and an autofluorescence method. Among these detection methods, the autofluorescence method makes it possible to obtain the result on the presence or absence of viable particles in real time. According to the autofluorescence method, a given substance is irradiated with light with to predetermined wavelength, and an enemy state of the substance is excited (the irradiation light is absorbed). Then, the substance emits extra energy as fluorescence to the outside when returning to a ground state. This phenomenon is used to detect the presence or absence of viable particles. Most of viable particles have a substance with such characteristic features (such as riboflavin). The autofluorescence method is intended to determine the presence or absence of stable particles depending on whether or not fluorescence is detected. In addition, by irradiating the substance by light at a wavelength inherent to the substance, autofluorescence can be selectively generated.

There is known a related art by which to determine the presence or absence of viable particles in water by means of this autofluorescence phenomenon (for example, see JP-A2009-501907: Patent Document 1). According to the related art, a water medium including viable particles is irradiated with ultraviolet light, and depending on whether autofluorescence is detected, the presence or absence of the viable particles is determined. According to the related art in particular, a filter for selecting a specific portion (wavelength range) of autofluorescence to be measured is used.

As in the foregoing related art, when water is irradiated with ultraviolet light for detection of viable particles using detect on of autofluorescence in the water as an index, Raman-scattered light with a longer wavelength than that of the ultraviolet light is generated. As a result, the Raman-scattered light from water is detected as well as the autofluorescence. It is therefore difficult to detect only the presence or absence of viable particles using autofluorescence as an index for detection. Even if a specific wavelength range of the autofluorescence is selected, there is a possibility that the Raman-scattered light from water with the same wavelength as that of the autofluorescence is also detected. Accordingly, it is difficult to detect the presence or absence of viable particles according to the foregoing related art.

In addition, viable particles of fungi emitting feeble autofluorescence, such as heterotrophic bacteria, may not be detected by a viable particle counter using detection of autofluorescence as an index.

Under such circumstances, there is demand for a technique for accurately counting viable particles even emitting feeble autofluorescence. Specifically, there is demand for a technique by which to irradiate viable particles with ultraviolet light before counting the viable particles by a viable particle counter to increase the emission intensity of autofluorescence emitted from the viable particles, thereby resulting in improvement of the signal-to-noise ratio.

CITATION LIST

Patent Literature

Patent Document 1: JP-A-2009-501907

SUMMARY OF INVENTION

The invention disclosed herein includes a system and a method described below. The method is realized by operation of the system.

A system includes: a viable particle counting means (viable particle counter) that counts viable particles existing in a fluid by irradiating the fluid containing target particles to be detected (sample fluid) with light at a predetermined wavelength (excitation light), separating selectively autofluorescence or phosphorescence emitted from the target particles by the radiated light, receiving the separated autofluorescence or phosphorescence, and determining that the target particles are the viable particles according to the received autofluorescence or phosphorescence; and a pre-stage irradiation means (pre-stage irradiation device) that irradiates the fluid with ultraviolet light in advance before the viable particle counting means irradiates the fluid with the light at the predetermined wavelength.

In the above system, the ultraviolet light emitted from the pre-stage irradiation means may have a wavelength range of 200 to 280 nm.

In the above system, the pre-stage irradiation means may irradiate the fluid with the ultraviolet light for a predetermined period of time.

In this case, the system includes at least the pre-stage irradiation device and the autofluorescence detection-type viable particle counter. The viable particle counter is configured to count viable particles in the sample fluid (air or liquid). Specifically, before irradiation by as laser diode included in the viable particle counter, the pre-stage irradiation device irradiates the sample fluid with ultraviolet light. The sample fluid irradiated with the ultraviolet light, flows into the viable particle counter. Then, the viable particles are counted. The viable particle counter is configured to detect autofluorescence or phosphorescence emitted from the viable particles due to the irradiation of the light with a predetermined wavelength (excitation light) by the laser diode. In such a manner, the viable particle counter counts the viable particles.

As described above, by irradiating the viable particles with ultraviolet light in the system, the light amount (light intensity) of the autofluorescence or phosphorescence emitted from the viable particles is increased and the signal-to-noise ratio is improved. Thus, the system can perform high-accuracy counting. This system is also usable for counting viable particles such as heterotrophic bacteria that cannot be counted by a conventional viable particle counter because of their feeble autofluorescence.

The system further includes a storage means (reservoir) that stores the fluid. The pre-stage irradiation means may irradiate the fluid in the storage means with the ultraviolet light for a predetermined period of time.

As described above, the pre-stage irradiation device in the system irradiates the sample fluid stored in the reservoir with ultraviolet light. Thus, an irradiation time necessary for counting the viable particles in the fluid by the viable particle counter can be ensured in the system.

The system farther includes a flow passage means that causes the fluid to flow. The pre-stage irradiation means may irradiate the fluid in the flow passage means with the ultraviolet light for to predetermined period of time.

As described above, the pre-stage irradiation unit irradiates the sample fluid with ultraviolet light while letting the sample fluid flowing continuously. Thus, the viable particles can be continuously counted in the system without taking a waiting time until the fluid is delivered into the viable particle counter.

In the above system, the flow passage means may be a hollow pipe formed in a spiral shape and the fluid may flow through the hollow pipe As described above, the viable particle counting system can be made compact by forming the hollow pipe in a spiral shape.

Effects of the Invention

According to the invention disclosed herein, it is possible to conduct extremely accurate counting even if the viable particles can only emit feeble autofluorescence. Specifically, such accurate counting can be materialized to improve the signal-to noise ratio with increasing the emission intensity of autofluorescence or phosphorescence from the viable particles, by irradiating the viable particles with ultraviolet light before counting the viable particles by the viable particle counter.

BRIEF DESCRIPTION OF THE DRAWINGS

FIG. 14 is a graph representing the correlation between autofluorescence counted value for irradiation tune of ultraviolet light and scattered light counted value for irradiation time of ultraviolet light concerning fungi forming a medium-sized yellow colony (C); and FIG. 15 is a graph representing the correlation between autofluorescence counted value for irradiation time of ultraviolet light and scattered light counted value for irradiation time of ultraviolet light concerning fungi forming a small-sized orange colony (D).

DESCRIPTION OF EMBODIMENTS

Embodiments will be described below with reference to the drawings.

[Viable Particle Counting System]

Figure 1:
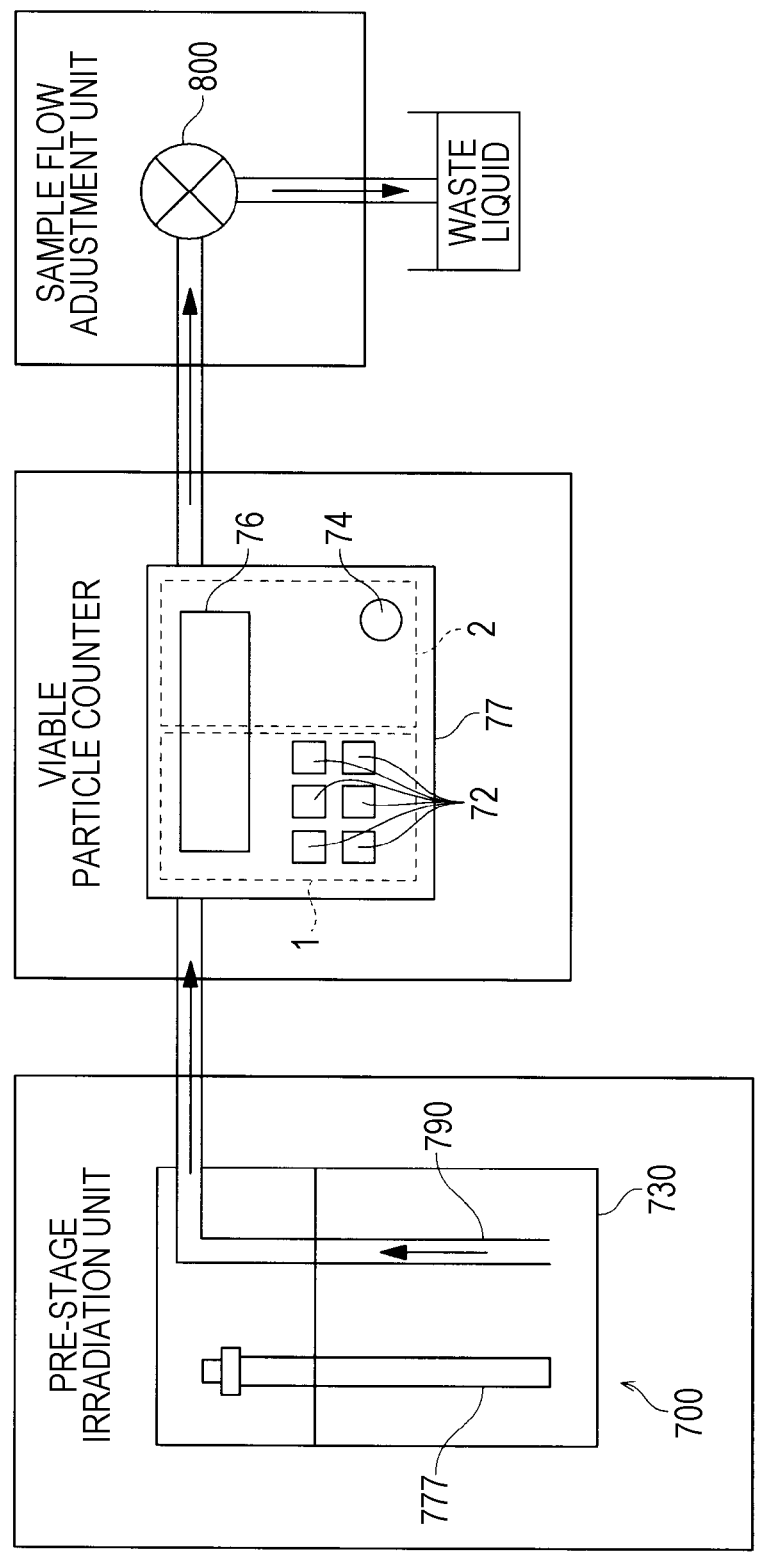
FIG. 1 is a schematic structure drawing of one embodiment of a viable particle counting system.

FIG. 1 is a schematic structure drawing of one embodiment of a viable particle counting system.

As illustrated in FIG. 1, the viable particle counting system includes a pre-stage irradiation unit 700, a viable particle counter 77, and a sample flow adjustment unit 800. Viable particles included in a sample liquid are counted at the viable particle counter 77. The pre-stage irradiation unit 700 is disposed upstream of the viable particle counter 77 relative to the sample liquid. The pre-stage irradiation unit 700 makes a preparation for increasing the light amount (light intensity) of autofluorescence or phosphorescence as an index for counting viable particles at the viable particle counter 77. The sample flow adjustment unit 800 adjusts the flow rate of the sample liquid flowing into the viable particle counter 77 (or flowing out of the viable particle counter 77). The sample liquid may include phosphorescence as well as autofluorescence.

Out of these elements constituting the viable particle counting system, first, the viable particle counter 77 will be described in detail. The viable particle counter 77 counts viable particles in the sample fluid using as an index of the detection of autofluorescence emitted from the viable particles irradiated with ultraviolet light. This description is based on the assumption that the sample fluid is water. Alternatively, the sample fluid may be air.

[Viable Particle Counter]

As illustrated in FIG. 1, the viable particle counter 77 includes a light detection unit 1 that irradiates a sample liquid (water) containing a target object (viable particles or non-viable particles) with excitation light and detects scattered light and autofluorescence from the target object; an autofluorescence counting unit 2 that counts the number of autofluorescence according to a signal output from the light detection unit 1; operation units 72 and 74; and a notification display 76. The operation units 72 and 74 include plural types of buttons, for example. The operation units 72 and 74 can accept operations of the viable particle counter 77. The notification display 76 can display, for example, input information, operation information, counting results, and the like. The viable particle counter 77 determines whether viable particles exist in the water irradiated in advance with ultraviolet light and fed from the pre-stage irradiation unit 700, and counts the viable particles when determining the viable particles exist.

Figure 2:
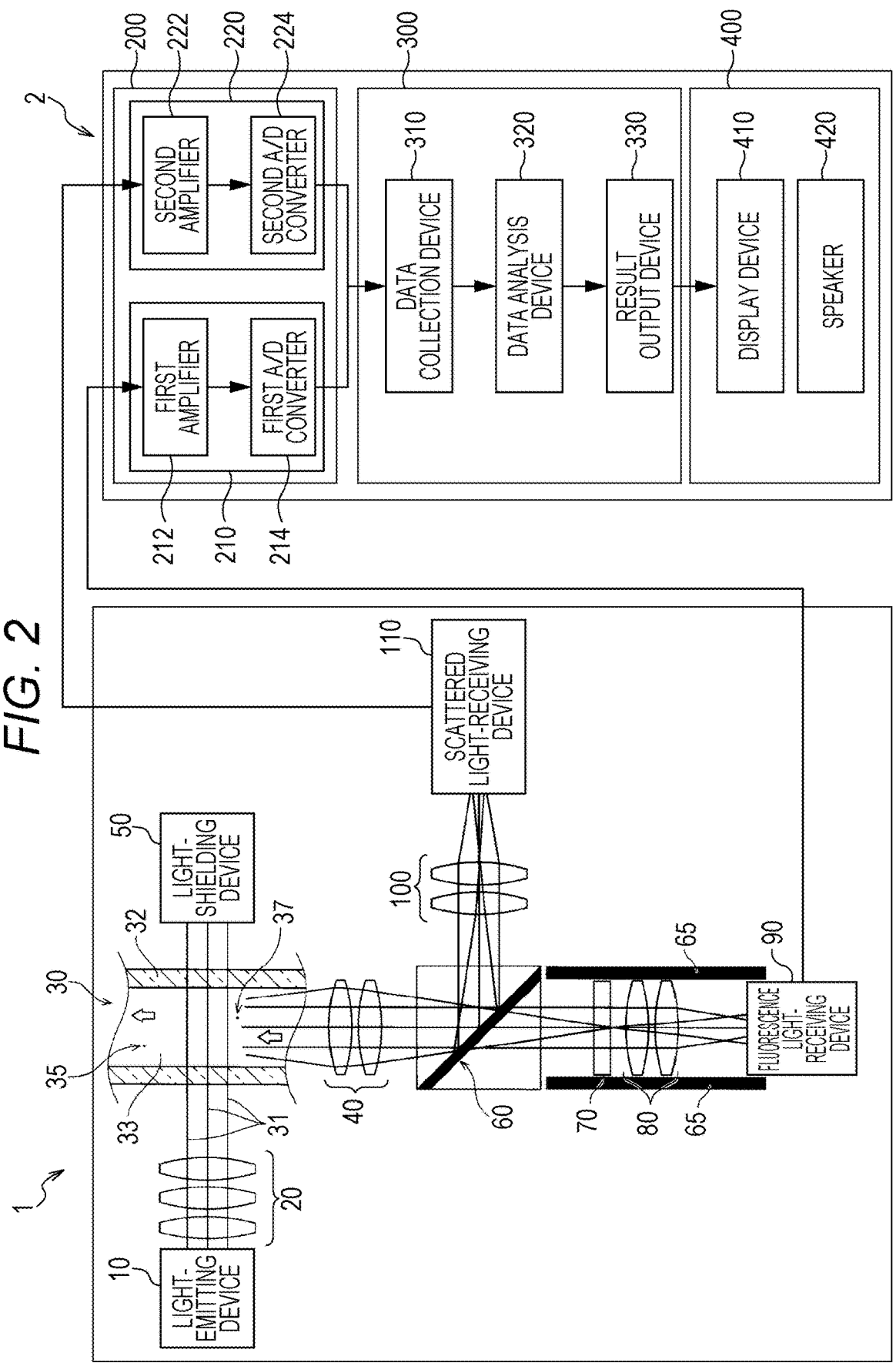
FIG. 2 is a schematic structure drawing of one embodiment of a viable particle counter.

FIG. 2 is a schematic structure drawing of one embodiment of the viable particle counter.

As illustrated in FIG. 2, the light detection unit 1 and the autofluorescence counting unit 2, which constitute the viable particle counter 77, detect and count viable particles of floating particles (target object) in the water. Viable particles detectable (countable) by the viable particle counter 77 independently in the embodiment are viable particles with sizes of 0.1 to several hundreds of μm, for example. Specifically, the detectable (countable) viable particles are bacteria, yeasts, molds, or the like. The excitation light irradiated to the viable particles is laser light with ranges from ultraviolet to green visible light. The viable particles are detected by using, as an index, autofluorescence emitted from substances necessary for metabolism (riboflavin, NAD (P)H (nicotinamide adenine dinucleotide (phosphate)), and the like) existing in the bodies (cells) of the viable particles.

[Light Detection Unit]

The light detection unit 1 includes: a light-emitting device 10; an irradiation optical lens system 20; a flow cell 32; a first light-collecting optical lens system 40; a light-shielding device 50; a scattered light selection optical device 60; a light-shielding wall 65; an autofluorescence selection optical device 70; a second light-collecting optical lens system 80; a fluorescence light-receiving device 90; a third light-collecting optical lens system 100; and a scattered light-receiving device 110, for example. These constituent elements make it possible to irradiate a target object with light and detect scattered light and autofluorescence from the target object. The constituent elements will be described below in detail.

[Light-Emitting Device]

The light-emitting device 10 is formed by a semiconductor laser (including a semiconductor LED element, hereinafter referred to as laser diode), for example. The laser diode irradiates water including viable particles with laser light (excitation light). The wavelength of the laser light to be emitted from the laser diode is decided according to a substance capable of emitting autofluorescence existing in the cells of the viable particles (hereinafter referred to as autofluorescent substance). The wavelength (excitation wavelength) with which the autofluorescent substance is likely to absorb energy of the radiated light and enter into the excited state differs depending on autofluorescent substances. In addition, the wavelength of autofluorescence emitted from the autofluorescent substance at the time of returning from the excited state to the ground state also differs depending on autofluorescent substances. Specific examples of excitation wavelengths and autofluorescence wavelengths of autofluorescent substances will be described.

[Excitation Wavelengths and Autofluorescence Wavelengths]

Figure 3:
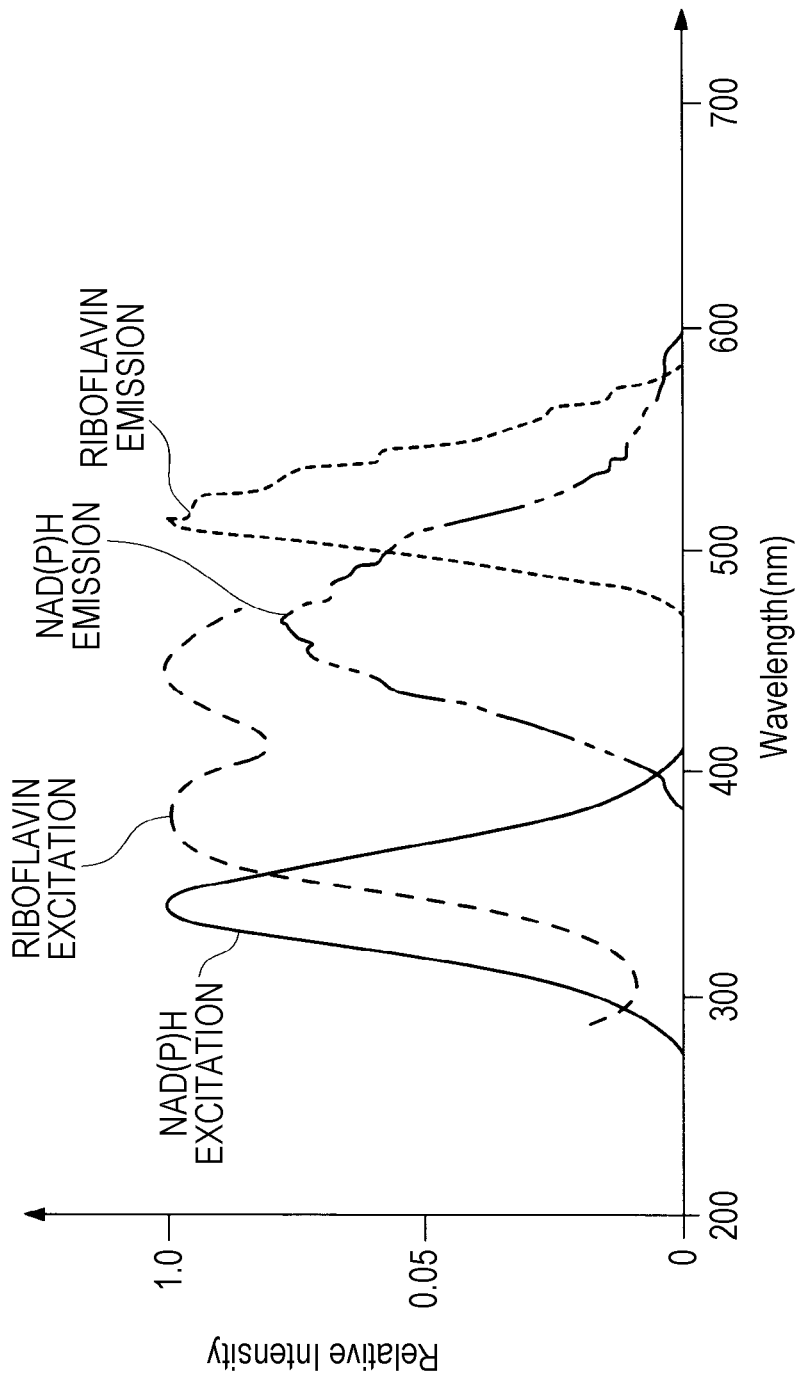
FIG. 3 is a chart of excited absorption spectra of riboflavin and NAD(P)H as examples of autofluorescent substances and autofluorescence spectra from the substances.

FIG. 3 is a chart illustrating an example of excited absorption spectra of autofluorescent substances and autofluorescence spectra from the substances.

Distributions in FIG. 3 are illustrated as an excited absorption spectrum of NAD(P)H, an excited absorption spectrum of riboflavin, an autofluorescence spectrum of NAD(P)H, and an autofluorescence spectrum of riboflavin. For example, the excited absorption spectrum of NAD(P)H exhibits the distribution with a wavelength of about 340 nm as a peak. The excited absorption spectrum of riboflavin exhibits the distribution with wavelengths of about 375 nm and 450 nm as peaks. FIG. 3 indicates that irradiation of laser light at a wavelength of 330 to 500 nm is suitable to make riboflavin likely to be excited, for example.

Therefore, the wavelength of laser light emitted from the laser diode for emission of much autofluorescence from the viable particles is decided according to the excitation wavelength of NAD(P)H or riboflavin existing in the cells of the viable particles. In the embodiment, the laser light at a wavelength of 405 nm is emitted from the laser diode. The irradiation of the laser light at the wavelength of 405 nm allows the viable particles to emit autofluorescence from riboflavin.

[Irradiation Optical Lens System]

The irradiation optical lens system 20 includes, for example, plural types of optical lenses. For example, the irradiation optical lens system 20 includes a collimator lens, a biconvex lens, and a cylindrical lens. The laser light emitted from the laser diode is adjusted to flat parallel light rays and irradiated to the target object.

[Flow Cell]

The flow cell 32 includes a square hollow column made of synthetic quartz or sapphire, for example. The flow cell 32 is structured such that water 33 containing the target object (viable particles 35 or non-viable particles 37) can flow from bottom to top. The laser light 31 emitted from the laser diode passes through a hollow region of the flow cell 32 where the water 33 flows, thereby forming a detection region (where the laser light 31 exists in the hollow region).

In the detection region, the laser light 31 interacts with the water (water molecules) 33 and the target object the viable particles 35 or the non-viable particles 37) flowing through the flow cell 32.

The wavelength of the laser light 31 entering the viable particles 35 is 405 nm. Accordingly, scattered light from the viable particles 35 is also emitted at a wavelength of 405 nm. As illustrated in FIG. 3, autofluorescence from the viable particles 35 exhibits a distribution with a wavelength of about 520 nm as a peak when the laser light 31 is absorbed in riboflavin in the cells of the viable particles 35. The scattered light or autofluorescence emitted from the viable particles 35 is released to the circumference through the flow cell 32.

The scattered light resulting from the laser light 31 entering the non-viable particles 37 is the same as the scattered light emitted from the viable particles 35.

As described above, the viable particles 35 and the non-viable particles 37 interact with the laser light 31 to emit the scattered light from the viable particles 35 and the non-viable particles 37 or the autofluorescence from the viable particles 35. Then, these lights pass through the plural light collection lens systems and wavelength selection optical devices, and are detected by the light-receiving device. The intensity of the scattered light, that is, the light amount of the scattered light depends on the sizes of the viable particles 35 and the non-viable particles 37. The larger the particles are in size, the more the light amount is increased. In this example, the light amount of the autofluorescence from the viable particles 35 depends on the amount of riboflavin in the cells of the viable particles 35. The light amount of the autofluorescence from the viable particles 35 also depends on the light amount (intensity) of the laser light 31. When laser power is increased to irradiate the flow cell 32 with a large amount of laser light 31, the scattered light from the viable particles 35 and the non-viable particles 37 and the autofluorescence from the viable particles 35 also increase. However, light (Raman-scattered light) resulting from the interaction (Raman scattering) between the laser light 31 and the water 33 also increases. Next, the Raman-scattered light resulting from the water will be described in detail.

[Raman-Scattered Light from Water]

Figure 4:
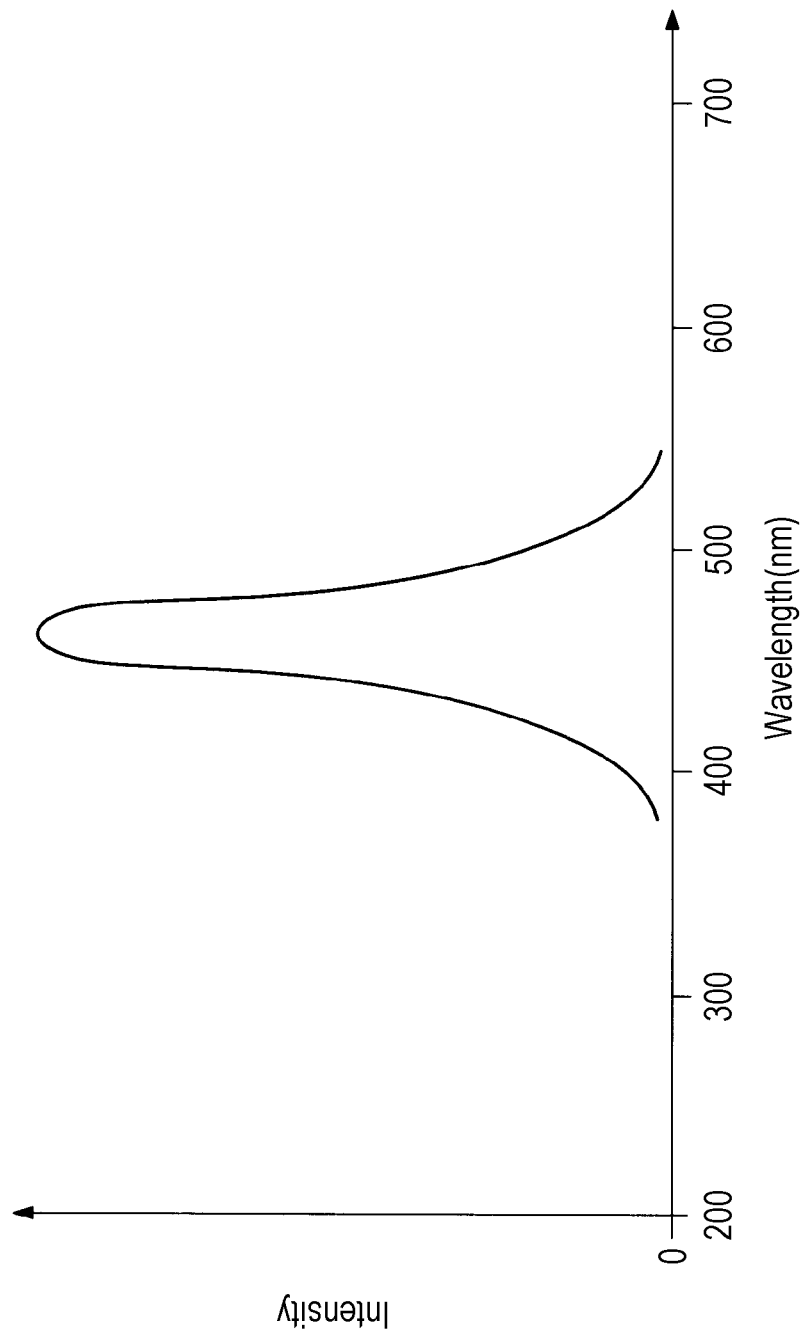
FIG. 4 is a chart illustrating a Raman-scattered light spectrum from water irradiated with light at a wavelength of 405 nm.

FIG. 4 is a chart of a Raman-scattered light spectrum resulting from water irradiated with light at a wavelength of 405 nm. As illustrated in FIG. 4, when the water is irradiated with the laser light 31 at a wavelength of 405 nm, the water and the laser light 31 interact with each other to emit Raman-scattered light having a wavelength distribution with as wavelength of about 465 nm as a peak.

[Light-Shielding Device]

The light-shielding device 50 shuts off the laser light 31 having been emitted from the laser diode and passed though the flow cell 32 without interaction. The light shielding suppresses that the passed laser light 31 causes noise which originates in reflection or the like and interferes with detection of scattered light and autofluorescence from the viable particles 35.

[First Light-Collecting Optical Lens System]

The first light-collecting optical lens system 40 includes plural optical lenses, for example. The first light-collecting optical lens system 40 is disposed at an angle of about 90 degree against the travel direction (optical axis) of the laser light 31. The first light-collecting optical lens system 40 collects the scattered light from the viable particles 35 and the non-viable particles 37 and the autofluorescence from the viable particles 35 in the flow cell.

[Scattered Light Selection Optical Device]

The scattered light selection optical device 60 includes a dichroic mirror, for example. The dichroic mirror in the embodiment allows light with wavelengths of 410 nm or more to pass therethrough and reflects light with wavelengths less than 410 nm. The specific wavelength as a reference for light separation will be referred to as a cutoff wavelength. Therefore, the wavelength of the scattered light from the viable particles 35 and the non-viable particles 37 caused by the laser light 31 with a wavelength of 405 nm in the flow cell is mainly 405 nm. Accordingly, the dichroic mirror reflects only the scattered light from the viable particles 35 and the non-viable particles 37. Then, the reflected scattered light from the viable particles 35 and the non-viable particles 37 is then collected by the third light-collecting optical lens system 100 to form an image at the scattered light-receiving device 110.

The autofluorescence emitted from the viable particles 35 flowing in the flow cell has a wavelength distribution with a wavelength of about 520 nm as a peak as illustrated in FIG. 3. Accordingly, almost all of the autofluorescence is not reflected on the dichroic mirror and passes through the dichroic mirror. Similarly, the Raman-scattered light from the water has a wavelength distribution with a wavelength of about 465 nm as a peak as illustrated in FIG. 4. That is, most of the Raman-scattered light has wavelengths that are longer than 410 nm of the cutoff wavelength. Accordingly, most of the Raman-scattered light from the water, excluding part of the Raman-scattered light, passes through the dichroic mirror. The passed autofluorescence and Raman-scattered light then move to the autofluorescence selection optical device.

The cutoff wavelength as a reference for the dichroic mirror is not limited to 410 nm. The wavelength only needs to allow reflection of the scattered light from the viable particles 35 or the non-viable particles 37 scattered by the laser light 31 and passage of the autofluorescence from the viable particles 35.

[Autofluorescence Selection Optical Device]

The autofluorescence selection optical device 70 includes an optical filter, for example. In the embodiment, the autofluorescence selection optical device 70 includes a long-path filter that allows light with wavelengths longer than 490 nm (cutoff wavelength) to pass therethrough.

As illustrated in FIG. 4, most of the Raman-scattered light from the water, excluding part of the Raman-scattered light, has wavelengths shorter than the cutoff wavelength of 490 nm, and accordingly, the Raman-scattered light is reduced by the long-path filter.

As a reference of a cutoff wavelength for light separation at the autofluorescence selection optical device 70, the cutoff wavelength that makes the Raman-scattered light from the water smaller than the autofluorescence emitted from the viable particles 35 is selected. Specifically, the cutoff wavelength is not limited to 490 nm, but may be any one of the wavelengths of 450 to 520 nm, preferably 450 to 490 nm. In addition, the long-path filter is not necessarily configured to allow light with wavelengths longer than 490 nm to pass therethrough, but the band-path filter may be configured to allow light within a wavelength range of 490 to 600 nm to pass therethrough.

As a modification example, a system is assumed to be configured such that the wavelength of the laser light 31 is set to about 350 nm and autofluorescence with a wavelength of about 470 nm as a peak is detected in order to count the viable particles 35 with the use of autofluorescence from NAD(P)H in the cells of the viable particles 35 as an index. In this case, the cutoff frequency for the scattered light selection optical device 60 is set to about 380 nm. The Raman-scattered light from the water has a distribution with about 400 nm as a peak. Accordingly, the autofluorescence selection optical device 70 may be a long-path filter that has a cutoff wavelength of 410 to 470 mm (for example, 450 nm) and allows light with wavelengths longer than the cutoff wavelength to pass therethrough. Alternatively, the autofluorescence selection optical device 70 may be a band-path filter that allows light within a wavelength range of 450 to 600 nm as the cutoff wavelength to pass therethrough.

[Second Light-Collecting Optical Lens System: Refer to FIG. 2]

The second light-collecting optical lens system 80 includes plural optical lenses, for example. The second light-collecting optical lens system 80 is disposed along the travel direction (optical axis) of light having passed through the long-path filter. The autofluorescence having passed through the long-path filter is collected at the second tight-collecting optical lens system 80, and an image is formed on a light incident plane of the fluorescence light-receiving device 90.

[Fluorescence Light-Receiving Device]

The fluorescence tight-receiving device 90 includes a semiconductor light-receiving, element (photo diode: PD) or a photo multiplier tube (PMT) more sensitive than the photo diode, for example. These photo diode and photo multiplier tube (hereinafter referred to as photo multiplier) convert the received light into electric current. In other words, the photo diode and photo multiplier output electric current corresponding to the amount of the received light. As the amount of the received light is larger, the amount of the electric current becomes larger. An electrical signal output from the fluorescence light-receiving device 90 is then input into the autofluorescence counting unit 2.

[Scattered Light-Receiving Device]

The scattered light-receiving device 110 includes a photo diode or a photo multiplier, for example. The light entered into the scattered light-receiving device 110 has a wavelength shorter than 410 nm reflected, on the dichroic mirror. Specifically, the light entered into the scattered light-receiving device 110 is the light scattered from the viable particles 35 and the non-viable particles 37 flowing in the flow cell. An output signal from the scattered light-receiving device 110 is then input into the autofluorescence counting unit 2.

[Autofluorescence Counting Unit: Refer to FIG. 2]

The autofluorescence counting unit 2 includes a detection signal processing unit 200, a data processing unit 300, and a notification unit 400, for example.

The detection signal processing unit 200 receives an output signal from the light detection unit 1, that is, an output signal from the fluorescence light-receiving device 90, and an output signal from the scattered light-receiving device 110, for example. The detection signal processing unit 200 amplifies the received signal and performs AD conversion on the analog signal into a digital signal.

The data processing unit 300, for example, determines whether an autofluorescence signal (signal A) and a scattered-light signal (signal B) subjected to AD conversion at the detection signal processing unit 200 includes a signal derived from the viable particles 35 in the water, that is, a signal resulting from autofluorescence. The data processing unit 300 outputs the determination results and the like.

The notification unit 400 notifies the results of the determination by the data processing unit 300 to the outside or outputs a notification signal to the outside, for example.

The constituent elements and their processes will be described below in detail.

[Detection Signal Processing Unit]

The detection signal processing unit 200 includes a fluorescence output signal processing device 210 and a scattered light output signal processing device 220, for example. The fluorescence output signal processing device 210 includes a first amplifier 212 and a first analog/digital converter 214, for example. The scattered light output signal processing device 220 includes a second amplifier 222 and a second analog/digital converter 224, for example.

[Data Collection Process]

At the fluorescence output signal processing device 210, the first amplifier 212 amplifies an output signal from the fluorescence light-receiving device 90. Then, the first analog/digital converter 214 converts the analog signal amplified by the first amplifier 212 into a digital signal (signal A).

Similarly, at the scattered light output signal processing device 220, the second amplifier 222 amplifies an output signal from the scattered light-receiving device 110. Then, the second analog/digital converter 224 converts the analog signal amplified by the second amplifier 222 into a digital signal (signal B).

Subsequently, the converted digital signals A and B are then input into a data analysis device 320.

[Data Analysis Device]

The data analysis device 320 includes a calculation circuit (for example, CPU) that analyzes data (signal A and signal B) stored in a memory and a memory (ROM) that stores (saves) calculation process contents (programs, threshold data, and others) in advance, for example.

[Analysis Process]

Figure 5:
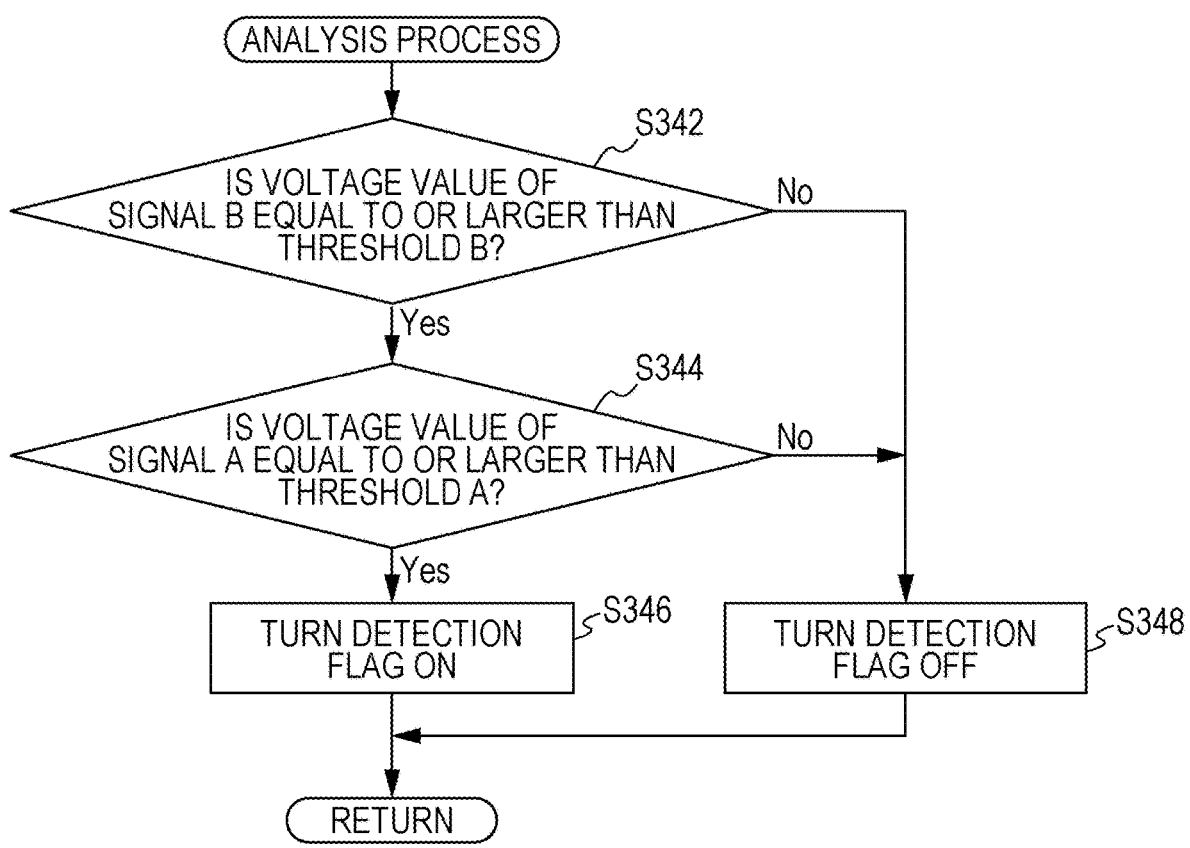
FIG. 5 is a flowchart of an example of an analysis process.

FIG. 5 is a flowchart of an example of an analysis process.

First, the signal B stored in the memory and the threshold data (voltage value) stored in advance in the memory by the CPU are compared to each other. Specifically, it is determined whether the voltage value of the stored signal B is equal to or higher than a threshold B (VthB) (step S342). When it is determined that the voltage value of the signal B is equal to or higher than the threshold B (step S342: Yes) as a result of the determination, this means that the scattered light-receiving device 110 has detected the scattered light from the viable particles 35 or the non-viable particles 37. Here, a scattered light detection flag may be turned on to indicate the detection of the scattered light from the viable particles 35 or the non-viable particles 37.

Next, the signal A stored in the memory and the threshold data (voltage value) stored in advance in the memory by the CPU are compared to each other. Specifically, it is determined whether the voltage value of the stored signal A is equal to or higher than a threshold A (VthA) (step S344). When it is determined that the voltage value of the signal A is equal to or higher than the threshold A (step S344: Yes) as a result of the determination, this means that the fluorescence light-receiving device 90 has detected the autofluorescence emitted from the viable particles 35. Then, a fluorescence detection flag is turned on to indicate the detection of the autofluorescence (step S346). The fluorescence detection flag (ON) is then transmitted as a flag signal to an analysis result output processing device 330.

In contrast, as a result of the determination, when it is determined that the voltage value of the signal B is not equal to or higher than the threshold B (step S342: No) or when it is determined that the voltage value of the signal A is not equal to or higher than the threshold A (step S344: No), the detection flag is turned of (step S348). This means that no autofluorescence has been detected. When the scattered light detection flag is on and the fluorescence detection flag is off, a non-viable particle detection flag may be turned on to indicate that the non-viable particles 37 have been detected instead of the viable particles 35. The fluorescence detection flag (OFF) is then transmitted as a flag signal to the analysis result output processing device 330. Further, the non-viable particle detection flag may be transmitted.

The analysis process will be described in detail with reference to the drawing of the signal A and the signal B corresponding to the output signals from the light-receiving devices.

[Example of Output Signals from Fluorescence Light-Receiving Device and Scattered Light-Receiving Device]

Figure 6:
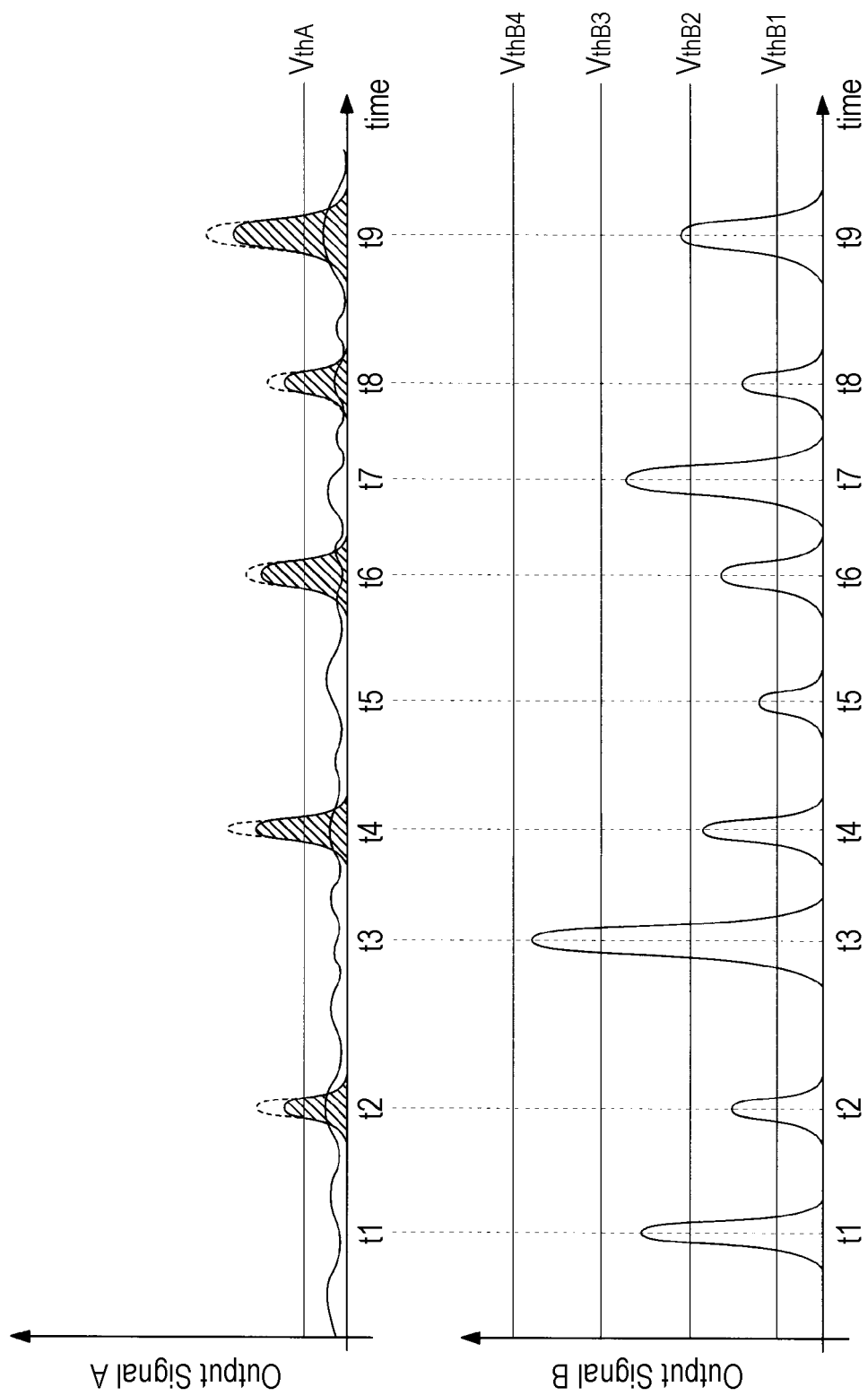
FIG. 6 is a chart of an example of output signals from a fluorescence light-receiving device and a scattered light-receiving device.

FIG. 6 is a chart illustrating an example of output signals from the fluorescence light-receiving device and the scattered light-receiving device.

The signal illustrated at the upper side of FIG. 6 indicates temporal changes in the signal A corresponding to a detection signal output from the fluorescence light-receiving, device 90. The signal illustrated at the lower side of FIG. 6 indicates temporal changes in the signal B corresponding to a detection signal output from the scattered light-receiving device 110. The signals A and B illustrated at the upper and lower sides of FIG. 6 are adjusted in timing.

For example, when the voltage value of the signal B higher than the threshold B (VthB (VthB1 in FIG. 6)) is input into the data processing unit 300 at time t1, the CPU determines that the voltage value of the signal B is higher than the threshold B (step S342: Yes). In other words, FIG. 6 indicates that the scattered light from the viable particles 35 or the non-viable particles 37 has been entered into the photo diode of the scattered light-receiving device and detected there at the time t1.

Then, the CPU compares the voltage value of the signal A to the threshold A (VthA) stored in advance in the memory by the CPU (step S344). At the time t1, the voltage value of signal A is not higher than the threshold A (step S344: No). Thus, the signal B at time t1 is regarded as scattered light from the non-viable particles 37. The fluorescence detection flag is turned off (step S348).

Next, at time t2, the CPU determines that the voltage value of the signal B is equal to or higher than the threshold B (step S342: Yes).

Then, the CPU compares the voltage value of the signal A to the threshold A (VthA) (step S344). As a result, the CPU determines that the voltage value of the signal A is equal to or higher than the threshold A (step S344: Yes). Therefore, the signal A and the signal B at the time t2 indicate the autofluorescence and scattered light from the viable particles 35. The fluorescence detection flag is turned on (step S346).

As described above, the result of the presence or absence of the viable particles 35 can be obtained in real time. The amounts of the signals A and B depend on the amounts of light entering the fluorescence light-receiving device 90 and the scattered light-receiving device 110. The amounts of the signals A and B and the amount of the scattered light depend on the size of the viable particles 35 or the non-viable particles 37. Therefore, it is possible to not only detect the presence or absence of the viable particles 35 but also count the viable particles 35 or the non-viable particles 37 by size according to the amounts of the signals A and B.

Here, it is assumed that the memory stores in advance plural thresholds (VthB1, VthB2, VthB3, VthB4, . . . ) for the signal B corresponding to the sizes of the viable particles 35 (0.1 to 0.3 µm, 0.3 to 0.5 µm, 0.5 to 1.0 µm, . . . ). For example, the signal B at the time t2 is higher than VthB1 and is lower than VthB2. Accordingly, the viable particles 35 can be counted as particles with sizes of 0.1 to 0.3 µm.

In addition, the amount of the signal A corresponding to the light amount of autofluorescence corresponds to the kind and active state of the viable particles. Accordingly, such information may be obtained b detecting the peak of the signal A.

As described above, the presence or absence of the viable particles 35 can be detected in real time according to the signals A and B. Furthermore, the sizes of the viable particles 35 can be measured. When the detection flag is turned on by the detection of the presence or absence of the viable particles 35, a process for counting the viable particles 35 is executed.

[Analysis Result Output Device]

The analysis result output device 330 is configured to count the number of the viable particles 35 analyzed by the data analysis device 320, and transmit the counted value to the notification unit 400.

[Notification Unit]

Figure 7:
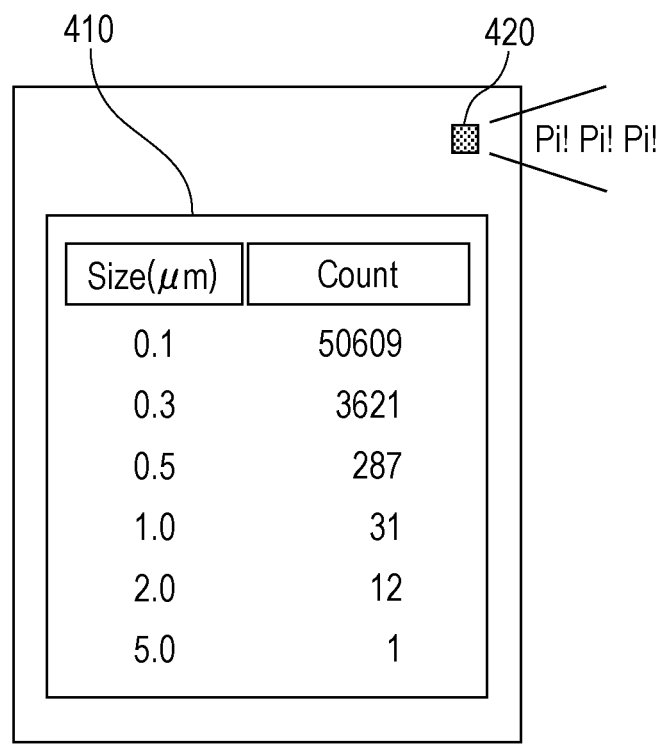
FIG. 7 is a view of an example of notification of counting results of viable particles.

FIG. 7 is a view illustrating an example of a display device and a speaker for notifying the counting result of the viable particles 35. The display device includes a display panel 410 that notifies the counting result of the viable particles 35 by size and a speaker 420 that notifies by sound that a predetermined number or more of viable particles 35 have been detected. For example, the display panel 410 includes a display unit of "Size(µm)" indicating a reference for size of the viable particles 35 and a display unit of "Count" indicating the number (counted value) of the viable particles 35 detected by size. The display unit of "Size(µm)" indicating a reference for size of the viable particles 35 displays in advance six values "0.1", "0.3,", "0.5", "2.0", and "5.0", for example. As to the individual values, "0.1" corresponds to the sizes of the viable particles 35 in the range of 0.1 to 0.3 µm, "0.3" corresponds to the sizes of the viable particles 35 in the range of 0.3 to 0.5 µm, "0.5" corresponds to the sizes of the viable particles 35 in the range of 0.5 to 1.0 µm, "1.0" corresponds to the sizes of the viable particles 35 in the range of 1.0 to 2.0 µm, "2.0" corresponds to the sizes of the viable particles 35 in the range of 2.0 to 5.0 µm, and "5.0" corresponds to the sizes of the viable particles 35 in the range of 5.0 µm and more.

Therefore, FIG. 7 indicates that the 50,609 viable particles 35 with sizes of 0.1 to 0.3 µm, the 3,621 viable particles 35 with sizes of 0.3 to 0.5 µm, the 287 viable particles 35 with sizes of 0.5 to 1.0 µm, the 31, viable particles 35 with sizes of 1.0 to 2.0 µm, the 12 viable particles 35 with sizes of 2.0 to 5.0 µm, and the one viable particle 35 with a site of 5.0 µm or more are respectively counted.

As described above, the notification unit 400 notifies the counted values of the viable particles 35 in real time on the display panel 410. When a predetermined number of viable particles 35 is detected, the speaker 420 can output a notification sound. Besides, the notification unit 400 may include an external output terminal. The notification unit 400 may output data to another device through the terminal.

As in the foregoing, according to the embodiment, the detection of autofluorescence from substances necessary for metabolism as in-vivo vital activity such as riboflavin and NAD(P)H in the cells of the viable particles 35 as a detection (measurement) target is used as an index. Then, the laser light 31 is irradiated at a wavelength corresponding to the substances. The dichroic mirror that reflects scattered light from the target object is provided. In addition, the long-path filter that reduces Raman-scattered light from the water or the like and allows autofluorescence from the viable particles 35 to pass therethrough is provided. In this manner, the viable particles 35 are counted. However, viable particles emitting only feeble autofluorescence such as heterotrophic bacteria may not be detected only by the viable particle counter described above.

[Sample Flow Adjustment Unit]

Next, the sample flow adjustment unit 800 as a constituent element of the viable particle counting system will be described.

The sample flow adjustment unit 800 causes a sample liquid, which is to be discharged from after the counting by the viable particle counter 77, to flow at a constant flow rate per unit time. For example, the sample flow adjustment unit 800 causes the sample fluid to flow from the viable particle counter 77 at a flow rate of 10 ml per minute.

[Pre-Stage Irradiation Unit]

Finally, the pre-stage irradiation unit 700 as a constituent element of the viable particle counting system will be described.

Figure 8:
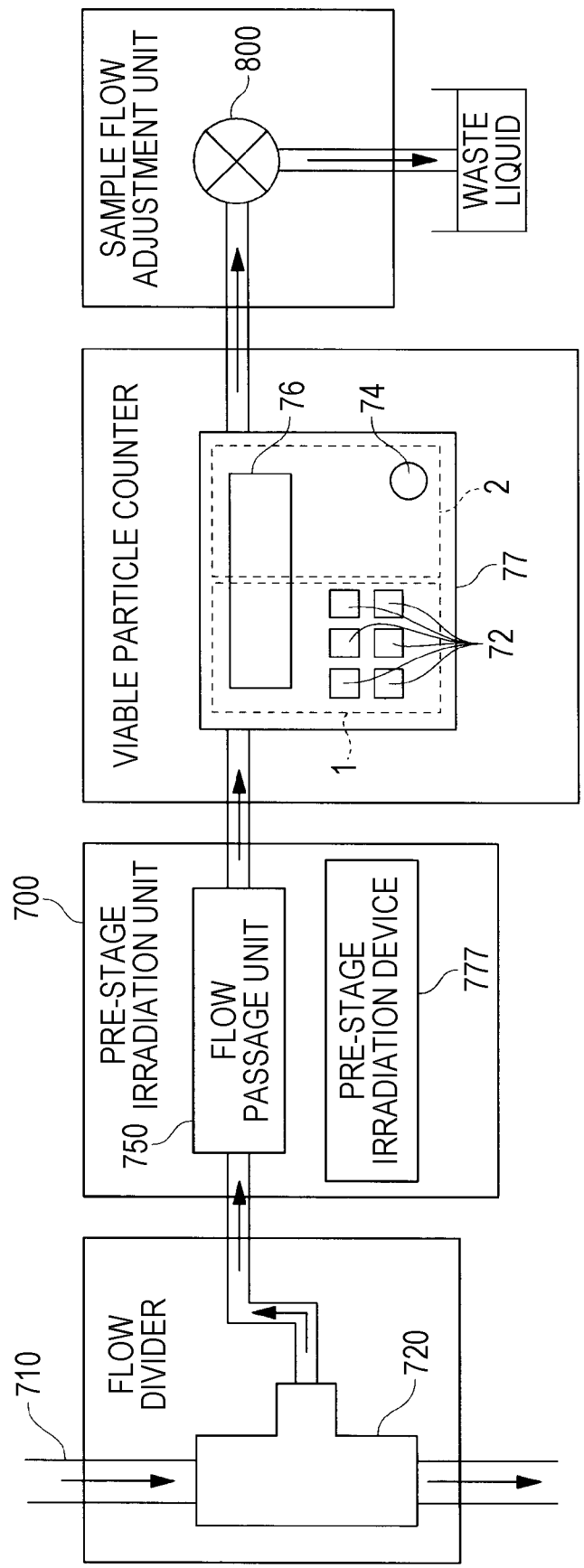
FIG. 8 is a schematic structure drawing of one embodiment of a viable counting system configured to count viable particles in a liquid using a continuous-type pre-stage irradiation unit.

The pre-stage irradiation unit 700 irradiates viable particles in the sample liquid flowing into the viable particle counter 77 with ultraviolet light for a predetermined period of time. The pre-stage irradiation unit 700 is broadly divided into a batch type and a continuous type as main types and either is adopted. The pre-stage irradiation unit illustrated in FIG. 1 is a batch type. In FIG. 8, a configuration of a continuous-type pre-stage irradiation unit is illustrated. Each type of the pre-stage irradiation units will be described below in detail.

[Batch-Type Pre-Stage Irradiation Unit]

As illustrated in FIG. 1, the hatch-type pre-stage irradiation unit 700 includes a reservoir 730, a pre-stage irradiation device 777, and a tube 790. The reservoir 730 temporarily stores the sample liquid before flowing into the viable particle counter 77. The pre-stage irradiation device 777 irradiates the sample liquid stored in the reservoir 730 with ultraviolet light at a predetermined intensity (illuminance) for a predetermined period of time. The sample liquid subjected to the irradiation of ultraviolet light by the pre-stage irradiation device 777 flows into the viable particle counter 77 through the tube 790. In the batch type, the measurement is completed for each predetermined amount. Accordingly, a constant amount of sample liquid is stored for each measurement. The stored sample liquid is irradiated with ultraviolet light. Subsequently, the viable particle counter 77 conducts counting. The constituent elements will be described below in detail.

[Reservoir (Storage Means)]

The reservoir 730 is formed by a container of quartz, for example. In this example, the pre-stage irradiation device 777 is disposed in the container. Alternatively, the pre-stage irradiation device 777 may be disposed outside the container because quartz is permeable to ultraviolet light. The material for the container is not limited to quartz, but may be any other material permeable to ultraviolet light. However, when the pre-stage irradiation device 777 is to be disposed in the container, the material for the container may not be permeable to ultraviolet light. The container may include a stir means for stirring the sample liquid so as to be evenly irradiated with ultraviolet light.

[Pre-Stage Irradiation Device (Pre-Stage Irradiation Means)]

The pre-stage irradiation device 777 includes an ultraviolet lamp or an ultraviolet LED configured to emit ultraviolet light, for example. The wavelength range (UV-C) of ultraviolet light ranges from 200 to 280 nm with a peak wavelength of around 250 nm exhibiting bactericidal activity against fungi. The light (electromagnetic wave) emitted from the pre-stage irradiation device 777 is not limited to ultraviolet light (UV-C), but may be any light (electromagnetic wave) with a wavelength capable of increasing the light amount (light intensity) such that the viable particle counter 77 can sufficiently detect autofluorescence or phosphorescence.

As illustrated in FIG. 1, the pre-stage irradiation device 777 is included in the container 730. Including the pre-stage irradiation device 777 in the container 730 allows irradiation of ultraviolet light to the sample liquid at close range. If the ultraviolet light to be irradiated has sufficient intensity, stains on the pre-stage irradiation device 777 and the like could be prevented by disposing an ultraviolet lamp outside the container 730.

The pre-stage irradiation device 777 increases the light amount (light intensity) of autofluorescence or phosphorescence emitted from the viable particles at the viable particle counter 77. However, the light amount depends on the kind of the viable particles to be counted. The irradiation time and irradiation strength (illuminance) per unit time of ultraviolet light are adjusted as appropriate.

A specific example of increasing the light amount (light intensity) of autofluorescence emitted from the viable particles at the viable particle counter 77 in the case of irradiating the viable particles in advance with ultraviolet light at the pre-stage irradiation device 777 will be explained with reference to Examples described below.

As described above, at the batch-type pre-stage irradiation unit 700, the sample fluid stored in the reservoir 730 is irradiated with ultraviolet light at the pre-stage irradiation device 777 for a predetermined period of time. After the irradiation, the sample liquid is flown from the tube 790 into the viable particle counter 77. Next, the continuous-type pre-stage irradiation unit 700 will be described.

[Continuous-Type Viable Particle Counting System]

FIG. 8 is a schematic structure drawing of one embodiment of a viable particle counting system configured to count viable particles in a liquid using a continuous-type pre-stage irradiation unit. The viable particle counter 77 and the sample flow adjustment unit 800 are the same as those in the batch-type pre-stage irradiation unit 700, and thus descriptions thereof will be omitted here.

As illustrated in FIG. 8, as an example, the water flowing through a water pipe 710 is divided by a flow divider 720 and flown into the continuous-type pre-stage irradiation unit 700. The sample liquid is irradiated with ultraviolet light at the continuous-type pre-stage irradiation unit 700, while flowing into the viable particle counter 77. In this example, these processes are continuously performed. The continuous-type pre-stage irradiation unit 700 includes a flow passage unit 750 and the pre-stage irradiation device 777. The pre-stage irradiation device 777 is the same as that in the batch-type pre-stage irradiation unit 700. In the embodiment, the viable particle counting system is configured to include the sample flow adjustment unit 800. However, the viable particle counting system may not include the sample flow adjustment unit 800 if the flow rate can be adjusted by the water pressure in the water pipe 710 or the flow divider 720.

[Continuous-Type Pre-Stage Irradiation Unit]

Figure 9:
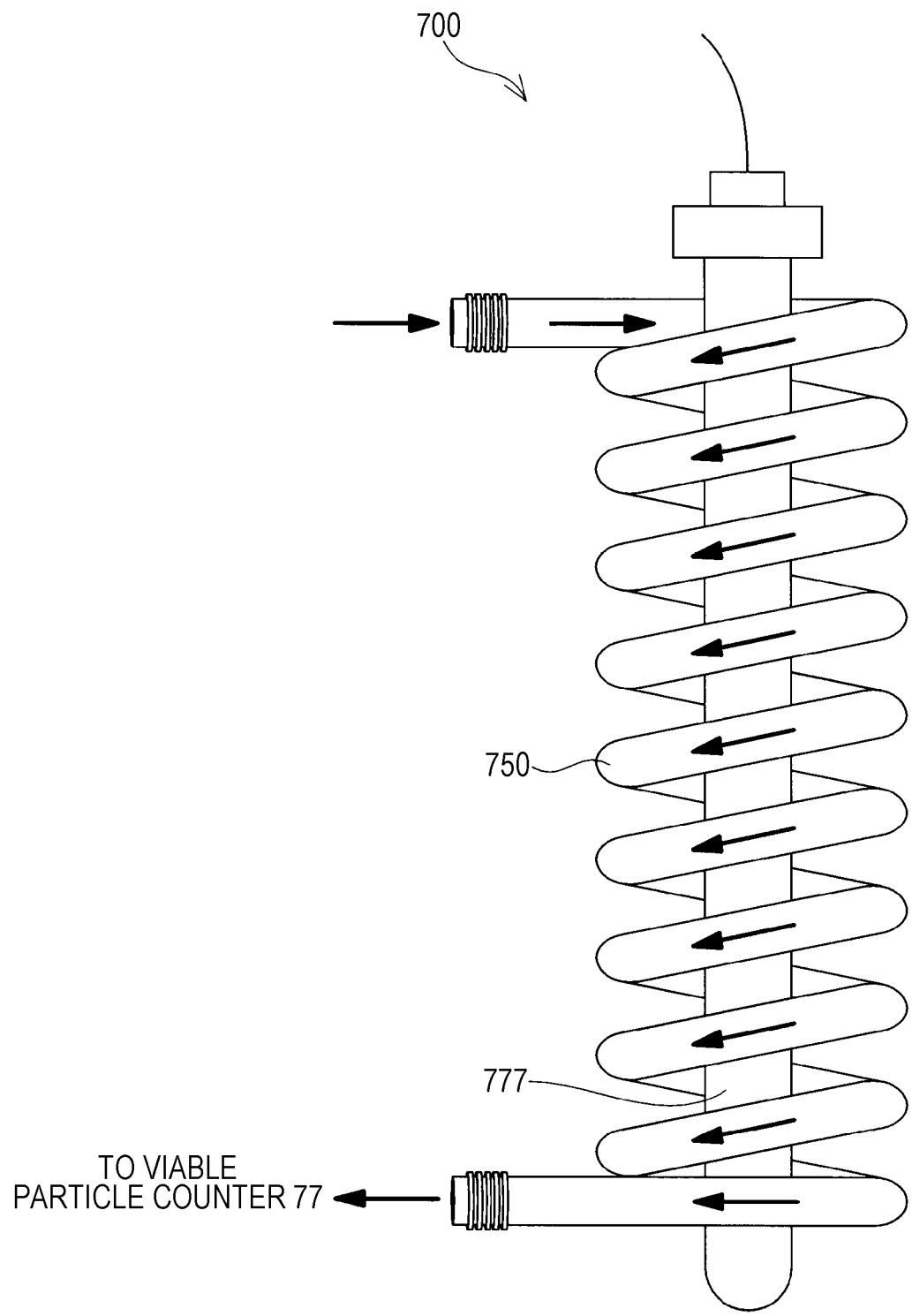
FIG. 9 is a schematic structure drawing of a configuration of the continuous-type pre-stage irradiation unit.

FIG. 9 is a schematic structure thawing illustrating the configuration of the continuous-type pre-stage irradiation unit.

As illustrated in FIG. 9, the flow passage unit 750 (flow passage means) are formed by a spiral-shaped quartz pipe, for example. The sample liquid flows in through one end of the quartz pipe. The sample liquid having irradiated with ultraviolet light by the pre-stage irradiation device 777 (pre-stage irradiation means) flows out of the other end of the quartz pipe. The outlet port of the quartz pipe is connected to the tube 790. Through the tube 790, the sample liquid flows into the viable particle counter 77. By forming the quartz pipe in a spiral shape, the pre-stage irradiation unit 700 can be made compact in the viable particle counting system. The shape of the quartz pipe may not be a three-dimensional spiral shape, but may be a zig-zag shape (not illustrated) bending and snaking alternately from side to side in a plane. The shape may be modified as appropriate as far as the flowing sample liquid can be irradiated by the pre-stage irradiation device 777 for a predetermined period of time.

Using the continuous-type pre-stage irradiation unit 700 with the configuration as described above makes it possible to irradiate the flowing sample fluid with ultraviolet light and deliver the sample fluid to the viable particle counter 77 immediately after completion of the irradiation for a predetermined period of time. In this manner, the viable particles contained in the tap water in the water pipe 710 can be continuously counted for a long time at the viable particle counter 77. Further, it is also possible to count viable particles contained in the liquid continuously not only through water pipe 710 but also in water treatment plant or the like with dividing the water by a pipe. As described above, the embodiment is useful for various applications.

In the foregoing case, the sample fluid is assumed as water. Even when the sample fluid is air, autofluorescence from the air can be detected in a similar manner.

Figure 10:
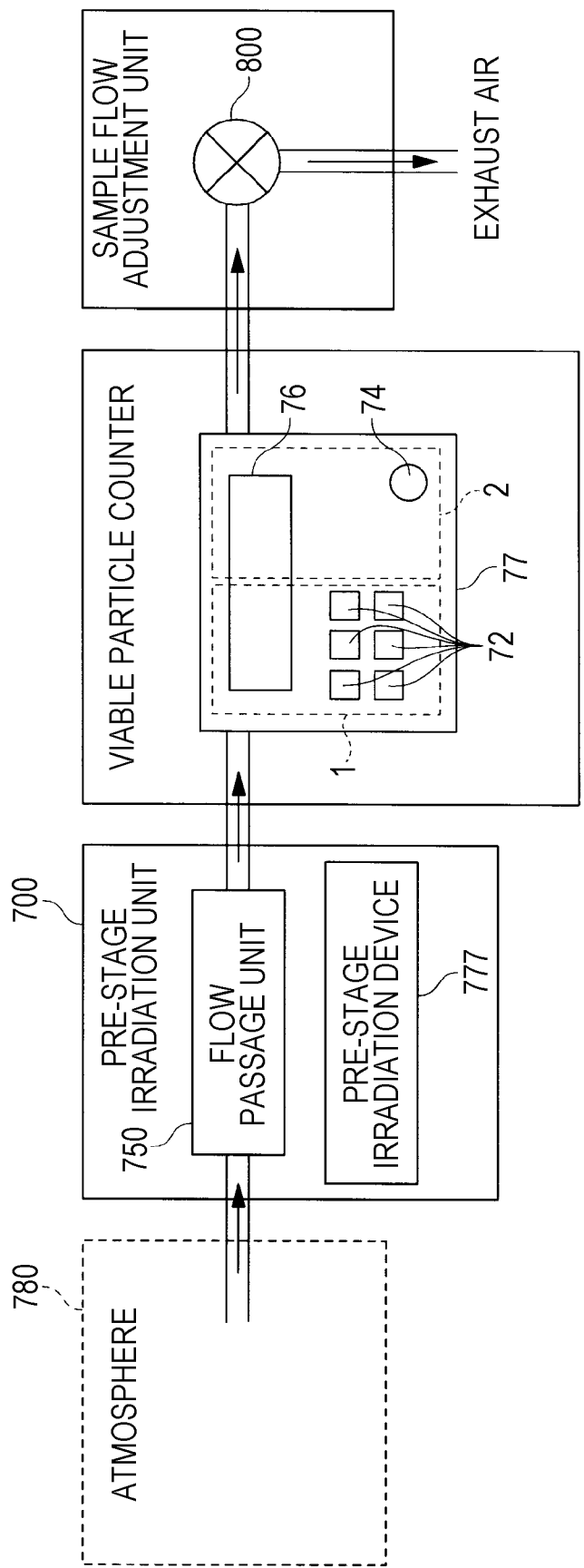
FIG. 10 is a schematic structure drawing of one embodiment of a viable particle counting system configured to count viable particles in the atmosphere using a continuous-type pre-stage irradiation unit.

FIG. 10 is a schematic structure drawing of one embodiment of a viable particle counting system configured to count viable particles in the atmosphere using the continuous-type pre-stage irradiation unit.

As illustrated in FIG. 10, as an example, the atmosphere 780 is absorbed as sample air and flown into the continuous-type pre-stage irradiation unit 700. At the continuous-type pre-stage irradiation unit 700, the sample air is irradiated with ultraviolet light while flowing into the viable particle counter 77. In this example, these processes are continuously performed.

The continuous-type pre-stage irradiation unit 700 for atmosphere includes the flow passage unit 750 (flow passage means) and the pre-stage irradiation device 777 (pre-stage irradiation means), in the same manner as the pre-stage irradiation unit 700 for liquid as described above. However, the sample flow adjustment unit 800 is provided with an air absorption pump. The viable particle counter 77 may not include the flow cell 32. If there is no influence of Raman-scattered light from the air, the light divided from the scattered light (reflected light) at the scattered light selection optical device 60 is only autofluorescence (passed light) from the viable particles 35. Accordingly, the autofluorescence selection optical device 70 may not be provided, but the fluorescence light-receiving device 90 may detect the autofluorescence.

Using the continuous-type pre-stage irradiation unit 700 with the configuration as described above makes it possible to irradiate the flowing air as well as the flowing liquid with ultraviolet light and deliver the air to the viable particle counter 77 immediately after completion of the irradiation for a predetermined period of time. In this manner, the viable particles contained in the atmosphere can be continuously counted at the viable particle counter 77 for a long time. For example, the air in a clean room can be absorbed to count continuously viable particles contained in the air. As described above, the embodiment is useful for various applications.

EXAMPLES

Examples of the disclosed invention will be described below in more detail. However, the disclosed invention is not limited to these examples. The embodiments of the disclosure can be modified as appropriate.

[Viable Particles]

Figure 11:
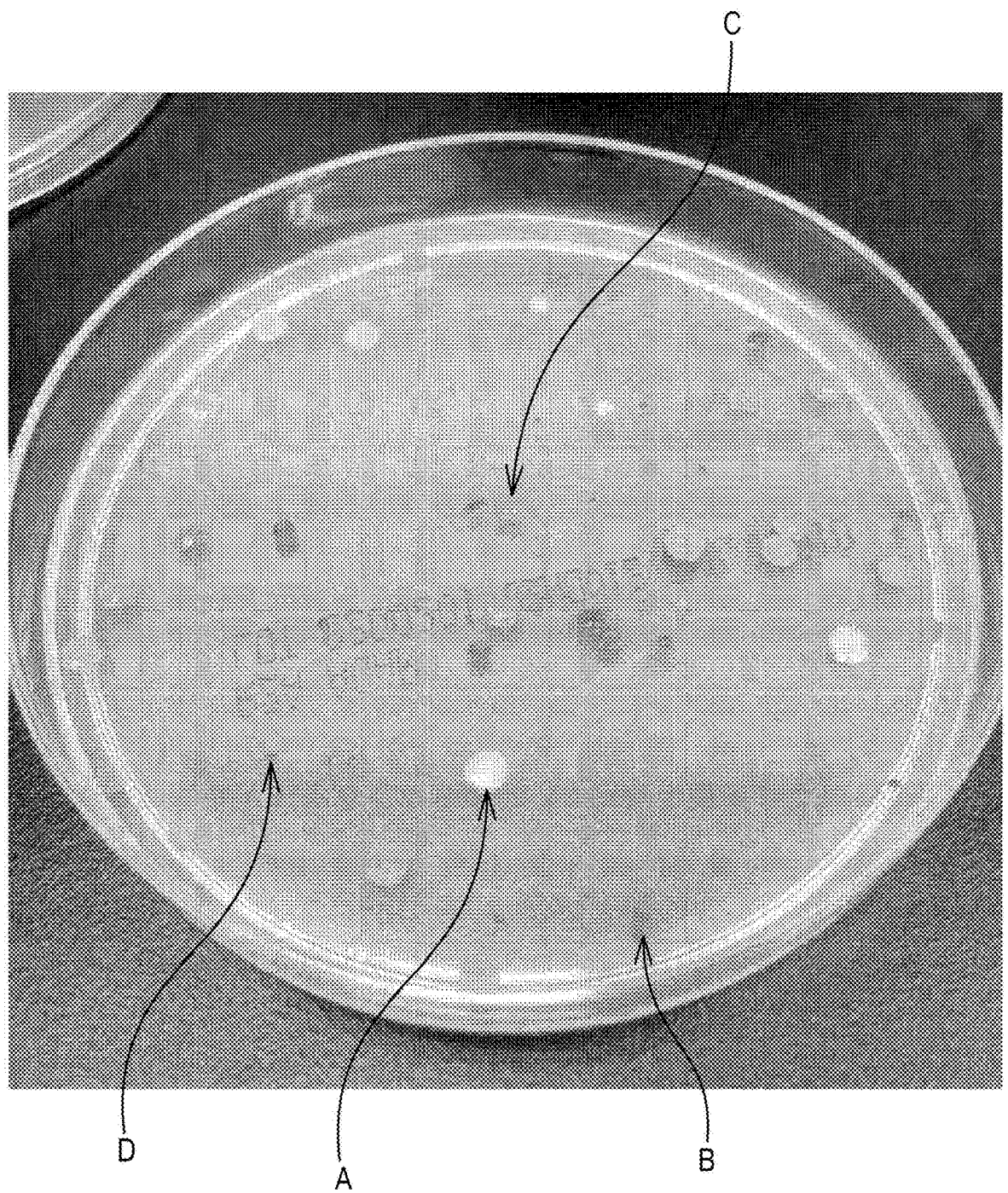
FIG. 11 is a drawing of plural kinds of fungi cultivated in the tap water.

FIG. 11 is a drawing of plural kinds of fungi cultivated in the tap water.

There exist plural kinds of fungi in the tap water. In FIG. 11, (A) denotes a large-sized white colony constituting a large-sized colony of white fungi, (B) denotes a medium-sized red colony constituting a medium-sized colony of red fungi, (C) denotes a medium-sized yellow colony constituting a medium-sized colony of yellow fungi, and (D) denotes a small-sized orange colony constituting a small-sized colony of orange fungi. The inventors have confirmed the effect of the disclosed invention with the use of these four kinds of fungi.

[Pre-Stage Irradiation Unit]

The pre-stage irradiation unit 700 is a batch-type pre-stage irradiation unit as illustrated in FIG. 1. Each of the four kinds of fungi (A) to (D) was put into the water. The pre-stage irradiation unit 700 includes the reservoir 730 (for example, beaker) storing the water, the pre-stage irradiation device 777 placed in the reservoir 730, and the tube 790 letting the waters, pass to the viable particle counter 77 after irradiation for a predetermined period of time.

[Pre-Stage Irradiation Device]

As the pre-stage irradiation device 777, an ultraviolet lamp with a peak wavelength of 253.7 nm in the wavelength range of ultraviolet light UV-C, a radiation output of 1.7 W, and a power consumption of 8 W was used.

[Sample Flow Adjustment Unit]

The sample flow adjustment unit 800 adjusted the flow rate at 10 ml per minute.

[Viable Particle Counter]

The viable particle counter 77 was used under the following conditions: as the light-emitting device 10, a laser diode with a peak wavelength of 405 nm was used; as the scattered light selection optical device 60, a dichroic mirror with a cutoff wavelength of 410 nm was used as the autofluorescence selection optical device 70, a band-path filter with a cutoff wavelength of 490 to 570 nm was used; as the fluorescence light-receiving device 90, a photo multiplier was used; and as the scattered light-receiving device 110, a photo diode was used.

Example 1

Of the four kinds of fungi, the large-sized white colony denoted by (A) in FIG. 11 was put into the water in the beaker and stirred there. The water was irradiated with ultraviolet light (UV-C) from the ultraviolet lamp, and the viable particles in the water were counted by the viable particle counter 77 after each irradiation time. Specifically, the inventors have confirmed the transition between the counted values corresponding to autofluorescence obtained with processing output signals from photo multiplier which received autofluorescence and the counted values corresponding to scattered light obtained with processing output signals from photo diode which received scattered light.

Figure 12:
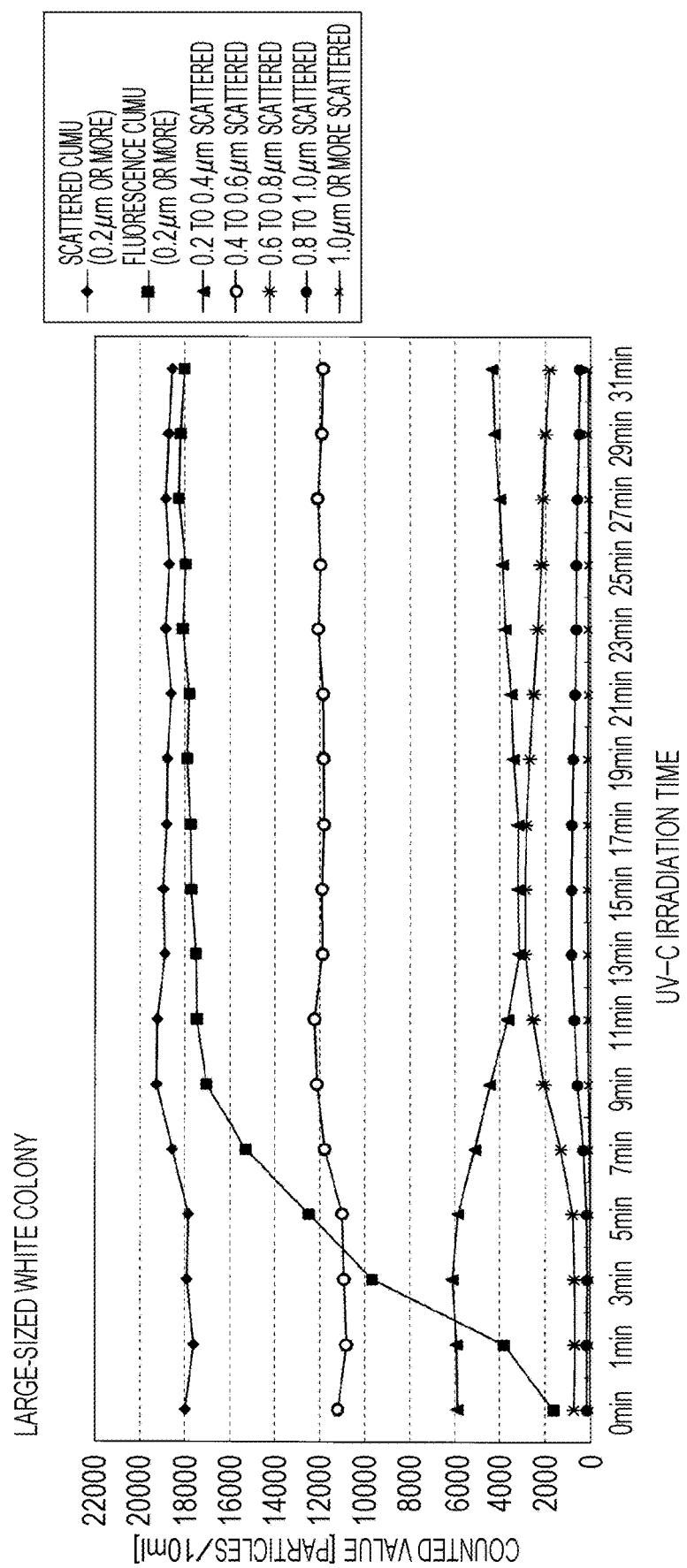
FIG. 12 is a graph representing the correlation between autofluorescence counted value for irradiation time of ultraviolet light and scattered light counted value for irradiation time of ultraviolet light concerning fungi forming a large-sized white colony (A)

FIG. 12 is a graph representing the correlation between autofluorescence counted value for irradiation time of ultraviolet light and scattered light counted value for irradiation time of ultraviolet light concerning fungi forming a large-sized white colony (A).

The lateral axis in FIG. 12 indicates the irradiation time of ultraviolet light (UV-C) from the ultraviolet lamp. The longitudinal axis in FIG. 12 indicates the counted value (particles/10 ml). In FIG. 12, for the scattered light, the counted values of the viable particles by particle diameter (for example, 0.2 to 0.4 μm, 0.4 to 0.6 μm, 0.6 to 0.8 μm, 0.8 to 1.0 μm, and 1.0 μm or more) are represented, and the cumulative number of the counted values is represented as scattered CUMU (0.2 μm or more). The counted value of the autofluorescence is represented as fluorescence CUMU (0.2 μm or more).

As illustrated in FIG. 12, before the irradiation of ultraviolet light (UV-C) by the ultraviolet lamp (0 min), the counted value of the scattered light (scattered CUMU) was about 18000 (particles/10 ml), whereas the counted value of the autofluorescence (fluorescence CUMU) was about 2000 (particles/10 ml). Therefore, considering that the counted value of the scattered light was obtained by detection of light emitted from all of the viable particles, the autofluorescence was hardly detected, which means that the actual number of the viable particles could not be counted.

With increase in the irradiation time of ultraviolet light (UV-C) from the ultraviolet lamp, the counted value of the autofluorescence (fluorescence CUMU) was increased with the irradiation time. Specifically, with regard to the relationship between the irradiation time of ultraviolet light (UV-C) and the counted value of the autofluorescence (fluorescence CUMU), the counted value was about 4000 (particles/10 ml) for one minute, the counted value was about 10000 (particles/10 ml) for three minutes; the counted value was about 12500 (particles/10 ml) for five minutes, the counted value was about 15000 (particles/10 ml) for seven minutes, the counted value was about 17000 (particles/10 ml) for nine minutes, and the counted value was about 17500 (particles/10 ml) for 11 minutes. Even when the ultraviolet light (UV-C) was emitted from the ultraviolet lamp for 13 minutes or longer, the counted value of the autofluorescence (fluorescence CUMU) was about 17500 to 18000 (particles/10 ml) and was not significantly increased.

Meanwhile, the counted value of the scattered light was almost constant without depending on the irradiation time of ultraviolet light (UV-C) from the ultraviolet lamp, and was about 18000 to 18500 (particles/10 ml).

In other words, when the ultraviolet (UV-C) was emitted from the ultraviolet lamp for at least 11 minutes, the counted value of the autofluorescence (fluorescence CUMU) became almost equal to the counted value of the scattered light (scattered CUMU). Since there was no increase or decrease in the counted number of viable particles, the viable particles incapable of being counted only by a viable particle counter due to their feeble fluorescence were counted by increasing the light amount (light intensity) of autofluorescence or phosphorescence from the viable particles.

Next, as Examples 2 to 4, the counted values of autofluorescence and scattered light from the fungi denoted by (B) to (D) in FIG. 11 relative to the irradiation time of ultraviolet light will be described. The measurement conditions used in Examples 2 to 4 are the same as those in Example 1, and thus descriptions thereof will be omitted.

Example 2

Figure 13:
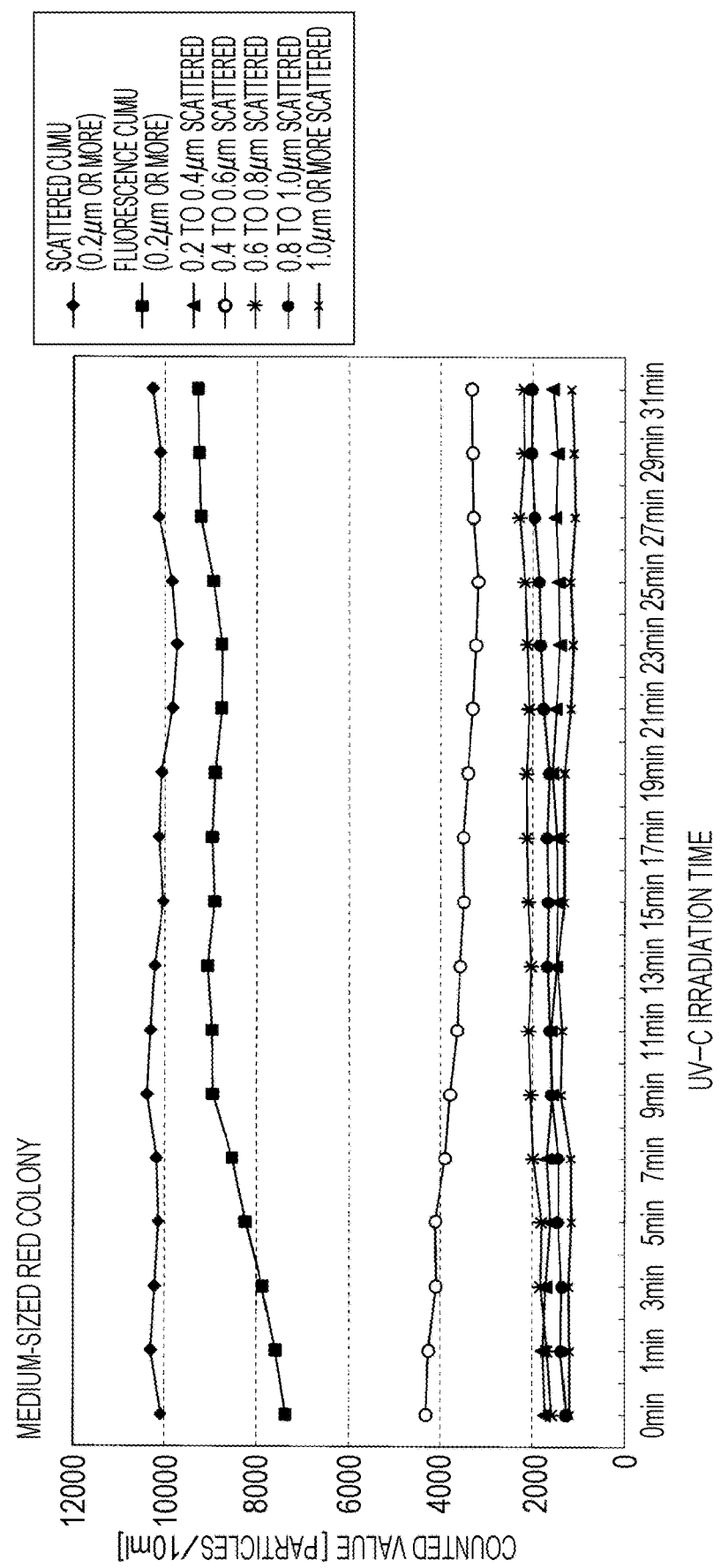
FIG. 13 is a graph representing the correlation between autofluorescence counted value for irradiation time of ultraviolet light and scattered light counted value for irradiation time of ultraviolet light concerning fungi forming a medium-sized red colony (B)

FIG. 13 is a graph representing the correlation between autofluorescence counted value for irradiation time of ultraviolet light and scattered light counted value for irradiation time of ultraviolet light concerning fungi forming a medium-sized red colony (B).

The lateral axis, the longitudinal axis, and the curve lines in the graph are the same as those in FIG. 12 described above, and descriptions thereof will be omitted (the same is applicable to FIGS. 14 and 15).

As illustrated in FIG. 13, before the irradiation of ultraviolet light (UV-C) by the ultraviolet lamp (0 mm), the counted value of the scattered light (scattered CUMU) was about 10000 (particles/10 ml), whereas the counted value of the autofluorescence (fluorescence CUMU) was about 7000 (particles/10 ml). Therefore, considering that the counted value of the scattered hat was obtained by detection of light emitted from all of the viable particles, autofluorescence could not be detected from some of the particles, which means that the actual number of the viable particles could not be counted.

With increase in the irradiation time of ultraviolet light (UV-C) from the ultraviolet lamp, the counted value of the autofluorescence (fluorescence CUMU) was increased with the irradiation time. Specifically, with regard to the relationship between the irradiation time of ultraviolet light (UV-C) and the counted value of the autofluorescence (fluorescence CUMU), the counted value was about 7500 (particles/10 ml) for one minute, the counted value was about 8000 (particles/10 ml) for three to five minutes, the counted value was about 8500 (particles/10 ml) for seven minutes, and the counted value was about 9000 (particles/10 ml) for nine minutes. Even when the ultraviolet light (UV-C) was irradiated from the ultraviolet lamp for 11 minutes or longer, the counted value of the autofluorescence (fluorescence CUMU) was about 9000 (particles/10 ml) and was not significantly increased.

Meanwhile, the counted value of the scattered light was almost constant without depending on the irradiation time of ultraviolet light (UV-C) from the ultraviolet lamp, and was about 10000 to 10500 (particles/10 ml).

In other words, when the ultraviolet light (UV-C) was emitted from the ultraviolet lamp for about nine minutes, the counted value of the autofluorescence (fluorescence CUMU) became almost equal to the counted value of the scattered light (scattered CUMU). Since there was no increase or decrease in the counted number of viable particles, the viable particles incapable of being counted only by a viable particle counter due to their feeble fluorescence were counted by increasing the light amount (light intensity) of autofluorescence or phosphorescence from the viable particles.

Example 3

FIG. 14 is a graph representing the correlation between autofluorescence counted value for irradiation time of ultraviolet light and scattered light counted value for irradiation time of ultraviolet light concerning fungi forming a medium-sized yellow colony (C).

As illustrated in FIG. 14, before the irradiation of ultraviolet light (UV-C) by the ultraviolet lamp (0 min), the counted value of the scattered light (scattered CUMU) was about 16500 (particles/10 ml), whereas the counted value of the autofluorescence (fluorescence CUMU) was about 2000 (particles/10 ml). Therefore, considering that the counted value of the scattered light was obtained by detection of light emitted from all of the viable particles, the autofluorescence was hardly detected, which means that the actual number of the viable particles could not be counted.

With increase in the irradiation time of ultraviolet light (UV-C) from the ultraviolet lamp, the counted value of the autofluorescence (fluorescence CUMU) was increased with the irradiation time. Specifically, with regard to the relationship between the irradiation time of ultraviolet light (UV-C) and the counted value of the autofluorescence (fluorescence CUMU), the counted value was about 6000 (particles/10 ml) for five minute, the counted value was about 11000 (particles/10 ml) for 11 minutes, the counted value was about 12000 (particles/10 ml) for 15 minutes, the counted value was about 15000 (particles/10 ml) for 21 minute, and the counted value was about 16000 (particles/10 ml) for 25 minutes. Even when the ultraviolet light (UV-C) was emitted from the ultraviolet lamp for 27 minutes or longer, the counted value of the autofluorescence (fluorescence CUMU) was about 16000 (particles/10 ml) and was not significantly increased.

Meanwhile, the counted value of the scattered light was almost constant without depending on the irradiation time of ultraviolet light (UV-C) from the ultraviolet lamp, and was about 16500 to 18000) (particles/10 ml).

In other words, when the ultraviolet light (UV-C) was emitted from the ultraviolet lamp for at least 25 minutes, the counted value of the autofluorescence (fluorescence CUMU) became almost equal to the counted value of the scattered light (scattered CUMU). Since there was no increase or decrease in the counted number of viable particles, the viable particles incapable of being counted only by a viable particle counter due to their feeble fluorescence were by increasing the light amount (light intensity) of autofluorescence or phosphorescence from the viable particles.

Example 4

FIG. 15 is a graph representing the correlation between autofluorescence counted value for irradiation time of ultraviolet light and scattered light counted value for irradiation time of ultraviolet light concerning fungi forming a small-sized orange colony (D).

As illustrated in FIG. 15, before the irradiation of ultraviolet light (UV-C) by the ultraviolet lamp (0 min), the counted value of the scattered light (scattered CUMU) was about 15500 (particles/10 ml), whereas the counted value of the autofluorescence (fluorescence CUMU) was about 200 (particles/10 ml). Therefore, considering that the counted value of the scattered light was obtained b detection of light emitted from all of the viable particles, the autofluorescence was hardly detected, which means that the actual number of the viable particles could not be counted.

With increase in the irradiation time of ultraviolet light (UV-C) from the ultraviolet lamp, the counted value of the autofluorescence (fluorescence CUMU) was increased with the irradiation time. Specifically, with regard to the relationship between the irradiation time of ultraviolet light (UV-C) and the counted value of the autofluorescence (fluorescence CUMU), the counted value was about 1000 (particles/10 ml) for five minute, the counted value was about 4000 (particles/10 ml) for 11 minutes, the counted value was about 7000 (particles/10 ml) for 15 minutes, the counted value was about 11000 (particles/10 ml) for 21 minutes, and the counted value was about 13000 (particles/10 ml) for 25 minutes. Even when the ultraviolet light (UV-C) was emitted from the ultraviolet lamp for 27 minutes or longer, the counted value of the autofluorescence (fluorescence CUMU) was about 13000 to 14000 (particles/10 ml) and was not significantly increased.

Meanwhile, the counted value of the scattered light was almost constant without depending on the irradiation time of ultraviolet light (UV-C) from the ultraviolet lamp, and was about 15000 to 15500 (particles/10 ml).

In other words, when the ultraviolet light (UV-C) was emitted from the ultraviolet lamp for at least 25 minutes, the counted value of the autofluorescence (fluorescence CUMU) became almost equal to the counted value of the scattered light (scattered CUMU). Since there was no increase or decrease in the counted number of viable particles, the viable particles incapable of being counted only by as viable particle counter due to their feeble fluorescence were counted by increasing the light amount (light intensity) of autofluorescence or phosphorescence from the viable particles.

As described above, in Examples 2 to 4, the viable particles (the fungi forming the medium-sized red colony, the medium-sized yellow colony, and the small-sized orange colony denoted by (B) to (D) in FIG. 11) contained in the sample fluids (waters) were successfully counted at the viable particle counter 77, as in Example 1. At that time, the sample fluids were irradiated with ultraviolet light (UV-C) by the ultraviolet lamp for predetermined periods of time (for at least nine minutes, 25 minutes, and 25 minutes corresponding to the individual fungi). As a result, in counting the viable particles at the viable particle counter 77, the light amount (light intensity) of autofluorescence or phosphorescence emitted from the viable particles was increased to improve the signal-to-noise ratio. Therefore, the viable particles incapable of being counted without irradiation of ultraviolet light (UV-C) were successfully counted. This enables high-accuracy counting of viable particles.

DESCRIPTION OF REFERENCE SIGNS

1 Light detection unit
2 Autofluorescence counting unit
10 Light-emitting device
20 Irradiation optical lens system
32 Flow cell
40 First light-collecting optical lens system
50 Light-shielding device
60 Scattered light selection optical device
65 Light-shielding Wall
70 Autofluorescence selection optical device
77 Viable particle counter
80 Second light-collecting optical lens system
90 Fluorescence light-receiving device
100 Third light-collecting optical lens system
110 Scattered light-receiving device
200 Detection signal processing unit
300 Data processing unit
400 Notification unit
700 Pre-stage irradiation unit
730 Reservoir
750 Flow passage unit
777 Pre-stage irradiation device
790 Tube
800 Sample flow adjustment unit

The invention claimed is:

1. A particle counting system configured to count target particles emitting autofluorescence and existing in a fluid, comprising:
   a particle counter configured to count the target particles existing in the fluid, the particle counter comprising:
      a light-emitting device configured to irradiate the fluid containing the target particles to be detected with light at a predetermined wavelength,
      an autofluorescence selection optical device configured to separate selectively the autofluorescence emitted from the target particles from the irradiated light,
      a fluorescence light-receiving device configured to receive the separated autofluorescence, and
      a data processing unit configured to compare a signal corresponding to the autofluorescence received by the fluorescence light-receiving device to a threshold data, determine a presence or an absence of the target particles according to a result of the comparison between the signal and the threshold data and count a number of the target particles existing in the fluid; and
   a pre-stage irradiation device configured to irradiate the fluid with ultraviolet light for a predetermined period of time such that a light intensity autofluorescence from the target particles in the particle counter increases as compared to a light intensity autofluorescence from the target particles in a case that the fluid is not irradiated with the ultraviolet light in advance, before the light-emitting device of the particle counter irradiates the fluid with the light at the predetermined wavelength,
   wherein the autofluorescence selection optical device of the particle counter comprises a band-pass filter that allows light having a wavelength of 450 nm to 600 nm to pass therethrough.

2. The particle counting system according to claim 1, wherein the ultraviolet light irradiated by the pre-stage irradiation device has a wavelength range of 200 to 280 nm.

3. The particle counting system according to claim 1, further comprising a reservoir configured to store the fluid, wherein
   the pre-stage irradiation device irradiates the fluid in the reservoir with the ultraviolet light for the predetermined period of time.

4. The particle counting system according to claim 1, further comprising a flow passage unit in which the fluid is capable of flowing, wherein
the pre-stage irradiation device is configured to irradiate the fluid flowing in the flow passage unit with the ultraviolet light for the predetermined period of time.

5. The particle counting system according to claim 4, wherein the flow passage unit is a hollow pipe having a spiral shape and the hollow pipe is configured to flow the fluid through the hollow pipe while the pre-stage irradiation device irradiates the fluid flowing in the hollow pipe with the ultraviolet light for the predetermined period of time.

6. The particle counting system according to claim 1, further comprising:
a scattered light selection optical device configured to separate selectively a scattered light from the target particles from the irradiated light, and
a scattered light-receiving device configured to receive the separated scattered light,
wherein the data processing unit is configured to compare a second signal corresponding to the scattered light received by the scattered light-receiving device to a second threshold data, and determine a size of the target particles according to the result of the comparison between the signal and the threshold data and a second result of the comparison between the second signal and the second threshold data.

7. A particle counting method for counting target particles emitting autofluorescence and existing in a fluid, comprising:
counting the target particles existing in the fluid, the counting comprises:
irradiating the fluid containing the target particles to be detected with light at a predetermined wavelength,
separating selectively the autofluorescence emitted from the target particles from the irradiated light by a band-pass filter that allows light having a wavelength of 450 nm to 600 nm to pass therethrough,
receiving the separated autofluorescence,
comparing a signal corresponding to the received autofluorescence to a threshold data, and
determining a presence or an absence of the target particles according to a result of the comparison between the signal and the threshold and counting a number of the target particles existing in the fluid; and
irradiating the fluid with ultraviolet light for a predetermined period of time such that a light intensity autofluorescence from the target particles at the counting increases as compared to a light intensity autofluorescence from the target particles in a case that the fluid is not irradiated with the ultraviolet light in advance, before irradiating the fluid with the light at the predetermined wavelength in the irradiating.

8. The particle counting method according to claim 7, wherein the ultraviolet light irradiated in the irradiating the fluid with ultraviolet light in advance has a wavelength range of 200 to 280 nm.

9. The particle counting method according to claim 7, further comprising storing the fluid while the fluid is irradiated with the ultraviolet light for the predetermined period of time in the irradiating the fluid with ultraviolet light in advance.

10. The particle counting method according to claim 7, wherein the irradiating the fluid with ultraviolet light in advance includes irradiating the fluid flowing in a flow passage unit with the ultraviolet light for the predetermined period of time.

11. The particle counting method according to claim 10, wherein, the flow passage unit is a hollow pipe formed in a spiral shape.

12. The particle counting method according to claim 7, further comprising determining the predetermined wavelength of the light irradiated in the counting according to an excitation wavelength of NAD(P)H or riboflavin existing in the target particles.

13. The particle counting method according to claim 7, further comprising:
separating selectively a scattered light from the target particles from the irradiated light,
receiving the separated scattered light,
comparing a second signal corresponding to the received scattered light to a second threshold data, and
determining a size of the target particles according to the result of the comparison between the signal and the threshold data and a second result of the comparison between the second signal and the second threshold data.

14. A particle counting method for counting target particles emitting autofluorescence and existing in a fluid, comprising:
irradiating the fluid containing the target particles to be detected with ultraviolet light;
determining a wavelength of light to be irradiated to the fluid which has been irradiated with ultraviolet light according to an excitation wavelength of NAD(P)H or riboflavin existing in the target particles; and
after irradiating the fluid with ultraviolet light, counting the target particles existing in the fluid,
wherein the counting comprises:
irradiating the fluid with light at the determined wavelength;
separating selectively the autofluorescence emitted from the target particles from the irradiated light by a band-pass filter that allows light having a wavelength of 450 nm to 600 nm to pass therethrough;
receiving the separated autofluorescence;
comparing a signal corresponding to the received autofluorescence to a threshold data; and
determining a presence or an absence of the target particles according to a result of the comparison between the signal and the threshold data, and counting a number of the target particles existing in the fluid.

15. The particle counting method according to claim 14, wherein the irradiating the fluid containing the target particles to be detected with ultraviolet light comprises irradiating the fluid with the ultraviolet light for a predetermined period of time such that a light intensity autofluorescence from the target particles in the counting increases as compared to a light intensity of autofluorescence from the target particles in a case that the fluid is not irradiated with the ultraviolet light.

16. The particle counting method according to claim 14, further comprising:
separating selectively a scattered light from the target particles from the irradiated light;
receiving the separated scattered light;
comparing a second signal corresponding to the received scattered light to a second threshold data; and determining a size of the target particles according to the result of the comparison between the signal and the threshold data and a second result of the comparison between the second signal and the second threshold data.

* * * * *